(12) United States Patent
Mazo et al.

(10) Patent No.: US 12,195,410 B2
(45) Date of Patent: Jan. 14, 2025

(54) NITRAPYRIN COMPOSITIONS FOR ENHANCING NITROGEN NUTRIENT USE EFFICIENCY AND IMPROVING PLANT GROWTH

(71) Applicant: Verdesian Life Sciences U.S., LLC, Cary, NC (US)

(72) Inventors: Jacob Mazo, Des Plaines, IL (US); Grigory Mazo, Des Plaines, IL (US)

(73) Assignee: Verdesian Life Sciences U.S., LLC, Cary, NC (US)

( * ) Notice: Subject to any disclaimer, the term of this patent is extended or adjusted under 35 U.S.C. 154(b) by 917 days.

(21) Appl. No.: 17/269,679

(22) PCT Filed: Aug. 26, 2019

(86) PCT No.: PCT/US2019/048155
§ 371 (c)(1),
(2) Date: Feb. 19, 2021

(87) PCT Pub. No.: WO2020/046819
PCT Pub. Date: Mar. 5, 2020

(65) Prior Publication Data
US 2021/0323890 A1    Oct. 21, 2021

Related U.S. Application Data

(60) Provisional application No. 62/723,284, filed on Aug. 27, 2018.

(51) Int. Cl.
| | | |
|---|---|---|
| *C05G 3/90* | (2020.01) | |
| *A01C 1/06* | (2006.01) | |
| *C05F 11/00* | (2006.01) | |
| *C08L 33/02* | (2006.01) | |

(52) U.S. Cl.
CPC ............... *C05G 3/90* (2020.02); *A01C 1/06* (2013.01); *C05F 11/00* (2013.01); *C08L 33/02* (2013.01)

(58) Field of Classification Search
None
See application file for complete search history.

(56) References Cited

U.S. PATENT DOCUMENTS

| | | |
|---|---|---|
| 3,135,594 A | 6/1964 | Goring |
| 9,637,420 B2 | 5/2017 | McKnight et al. |
| 2015/0105478 A1 | 4/2015 | van der Krieken et al. |
| 2016/0060184 A1* | 3/2016 | Gabrielson .............. C05G 3/90 71/30 |
| 2016/0102027 A1 | 4/2016 | Sanders et al. |
| 2016/0174547 A1 | 6/2016 | Sanders et al. |
| 2016/0192643 A1 | 7/2016 | Stark et al. |
| 2016/0332930 A1 | 11/2016 | Dave et al. |
| 2016/0332931 A1 | 11/2016 | Dave et al. |
| 2017/0183492 A1 | 6/2017 | Sanders et al. |
| 2017/0369386 A1 | 12/2017 | Dave et al. |
| 2018/0049438 A1 | 2/2018 | Dave et al. |
| 2018/0162783 A1* | 6/2018 | McKnight ................ C05G 5/37 |

FOREIGN PATENT DOCUMENTS

| | | |
|---|---|---|
| WO | 2011016898 A3 | 10/2011 |
| WO | 2015031521 A1 | 3/2015 |

OTHER PUBLICATIONS

International Search Report and Written Opinion for PCT/US2019/048155, with a mailing date of Dec. 13, 2019.

\* cited by examiner

*Primary Examiner* — Wayne A Langel
(74) *Attorney, Agent, or Firm* — Katten Muchin Rosenman LLP

(57) ABSTRACT

The presently disclosed subject matter is directed to nitrapyrin complexes and syntheses thereof finding particular utility in agricultural uses, e.g., directly applied to soil, or in combination with fertilizers to increase nutrient uptake and to inhibit nitrification and urease hydrolysis. More particularly, the subject matter is directed to nitrapyrin complexes, preferably containing specific types of carboxylic and sulfonate repeat units. Other uses of the nitrapyrin complexes and compositions containing nitrapyrin complexes are also disclosed.

20 Claims, No Drawings

NITRAPYRIN COMPOSITIONS FOR ENHANCING NITROGEN NUTRIENT USE EFFICIENCY AND IMPROVING PLANT GROWTH

CROSS-REFERENCE TO RELATED APPLICATIONS

This application is a US. National Stage entry of International Application No. PCT/US2019/048155 filed Aug. 26, 2019, which claims the benefit of U.S. patent application Ser. No. 62/723,284 filed Aug. 27, 2018, each of which is herein incorporated by reference in its entirety for all purposes.

FIELD

The presently disclosed subject matter is directed to nitrapyrin complex substances with polyanions and syntheses thereof finding particular utility in agricultural uses to increase nutrient uptake and to inhibit nitrification.

BACKGROUND

Nitrogen fertilizer added to the soil is readily transformed through a number of biological and chemical processes, including nitrification, leaching, and evaporation. Many transformation processes are undesirable because they reduce the level of nitrogen available for uptake by the targeted plant. The decrease in available nitrogen requires the addition of more nitrogen rich fertilizer to compensate for the loss of agriculturally active nitrogen available to the plants. Nitrification is the process by which certain widely occurring soil bacteria metabolize the ammonium form of nitrogen in the soil transforming the nitrogen into nitrite and nitrate forms, which are more susceptible to nitrogen loss through leaching or volatilization via denitrification. These concerns require improved management of nitrogen for economic efficiency and protection of the environment.

Nitrogen nutrient use efficiency enhancing compounds attempt to reduce nitrification. These so-called nitrification inhibitors have been developed to inhibit nitrogen loss due to nitrification. One class of nitrification inhibitors in use is composed of various chlorinated compounds related to pyridine, as taught by Goring in U.S. Pat. No. 3,135,594 (incorporated herein in its entirety by reference). Nitrapyrin is an example of a nitrification inhibitor.

Current formulations consist of nitrapyrin dissolved in large volumes of volatile, flammable, toxicologically problematic, environmentally problematic, and/or highly odoriferous aromatic solvents (e.g., toluene, xylenes, etc.). For every unit weight of nitrapyrin delivered to the field, more than 3-4 unit weights of such solvents are also delivered to the same soil. The relatively low concentration of active ingredient contributes to increased shipping costs, increased difficulty of handling, and reduced efficiency. Furthermore, once nitrapyrin has been employed, it suffers from significant losses to the atmosphere, resulting in undesirable environmental effects, loss of efficacy of product by way of potency loss, and offensive odors.

It is desirable to find a way to depress nitrapyrin volatilization without resorting to costly techniques. Further, is it desirable to replace current products with formulations that are more economical, less toxic, and less harmful to the environment.

BRIEF SUMMARY

In one aspect, the subject matter described herein is directed to nitrapyrin complex substances with polyanions, various uses of the nitrapyrin complexes, alone or in conjunction with other compounds. The polyanion can be a polyanionic polymer or a non-polymeric molecule having two or more negatively charged groups. Negatively charge groups include, but are not limited to, carboxyl groups, sulfonate groups, phosphonate groups, and mixtures thereof.

In one aspect, the subject matter described herein is directed to a composition comprising an agricultural product and a nitrapyrin complex with a polyanion(s).

In one aspect, the subject matter described herein is directed to a composition comprising a nitrapyrin complex with a polyanion(s), and an organic solvent, wherein the concentration of nitrapyrin is above about 20% wt.

In some embodiments, the disclosed nitrapyrin complex exhibit decreased volatilization in appropriate solvents when compared to nitrapyrin alone dissolved in solvent or when compared to known commercial nitrapyrin formulations.

In some embodiments, the subject matter described herein is directed to formulations suitable for use in agriculture, where the formulations comprise a described nitrapyrin complex.

In some embodiments, the subject matter described herein is directed to methods of increasing plant growth, yields and health, by contacting a composition comprising a described nitrapyrin complex with the plant or soil in the area of the plant.

In some embodiments, the subject matter described herein is directed to methods of decreasing nitrification and/or reducing atmospheric ammonia.

In some embodiments, the subject matter described herein is directed to methods of preparing the disclosed nitrapyrin complexes and compositions and formulations containing a nitrapyrin complex.

These and other aspects are fully described below.

DETAILED DESCRIPTION

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Advantageously, the compositions and methods described herein have been shown to provide desirable properties for the use of nitrapyrin in agriculture by formulating nitrapyrin complexes with polyanions. The properties include, but are not limited to: low cost, higher actives content relative to marketed products, ease of preparation, excellent environmental and toxicology profiles, and non-liquid dosage forms. As disclosed herein, among other properties, the nitrapyrin complexes have significantly lower vapor pressure, thereby reducing volatilization; increased solubility, thereby providing compositions with high loading and/or concentration; and increased stability when formulated in an environment with reduced water content.

Heretofore, methods found in the art for reducing volatility of materials involving pyridine derivatives involved an opposite approach. For example, the use of poly(4-vinylpyridine) sulfur trioxide complex is known to the art of sulfonation chemistry, wherein the volatility of sulfur trioxide is controlled by formation of a complex with poly(vinylpyridine). In this example, the pyridine derivative part of the molecule is the non-volatile portion, whereas the sulfur trioxide is the volatile portion. By contrast, a distinctly different approach as described herein utilizes nitrapyrin complexes with polyanions as a non-volatile component and a pyridine derivative, such as nitrapyrin as a volatile component.

I. Definitions

As used herein, the term "complex" or "complex substance" refers to chelates, coordination complexes, and salts of nitrapyrin, wherein nitrapyrin associates with functional groups of polyanion(s) in a covalent (i.e., bond forming) or non-covalent (i.e., ionic) manner. In a complex a central moiety or ion (e.g., nitrapyrin) associates with a surrounding array of bound molecules or ions known as ligands or complexing agents (e.g., polyanion(s)). The central moiety binds to or associates with several donor atoms of the ligand, wherein the donor atoms can be the same type of atom or can be a different type of atom. Ligands or complexing agents bound to the central moiety through several of the ligand's donor atoms forming multiple bonds (i.e., 2, 3, 4 or even 6 bonds) is referred to a polydentate ligand. Complexes with polydentate ligands are called chelates. Typically, complexes of central moieties with ligands are increasingly more soluble than the central moiety by itself because the ligand(s) that surround(s) the central moiety do not dissociate from the central moiety once in solution and solvates the central moiety thereby promoting its solubility.

As used herein, the term "salt" refers to chemical compounds consisting of an assembly of cations and anions. Salts are composed of related numbers of cations (positively charged ions) and anions (negative ions) so that the product is electrically neutral (without a net charge). Many ionic compounds exhibit significant solubility in water or other polar solvents. The solubility is dependent on how well each ion interacts with the solvent.

As used herein, the term "soil" is to be understood as a natural body comprised of living (e.g., microorganisms (such as bacteria and fungi), animals and plants) and non-living matter (e.g., minerals and organic matter (e.g., organic compounds in varying degrees of decomposition), liquid, and gases) that occurs on the land surface, and is characterized by soil horizons that are distinguishable from the initial material as a result of various physical, chemical, biological, and anthropogenic processes. From an agricultural point of view, soils are predominantly regarded as the anchor and primary nutrient base for plants (plant habitat).

As used herein, the term "fertilizer" is to be understood as chemical compounds applied to promote plant and fruit growth. Fertilizers are typically applied either through the soil (for uptake by plant roots) or by foliar feeding (for uptake through leaves). The term "fertilizer" can be subdivided into two major categories: a) organic fertilizers (composed of decayed plant/animal matter) and b) inorganic fertilizers (composed of chemicals and minerals). Organic fertilizers include manure, slurry, worm castings, peat, seaweed, sewage, and guano. Green manure crops are also regularly grown to add nutrients (especially nitrogen) to the soil. Manufactured organic fertilizers include compost, blood meal, bone meal and seaweed extracts. Further examples are enzymatically digested proteins, fish meal, and feather meal. The decomposing crop residue from prior years is another source of fertility. In addition, naturally occurring minerals such as mine rock phosphate, sulfate of potash and limestone are also considered inorganic fertilizers. Inorganic fertilizers are usually manufactured through chemical processes (such as the Haber-Bosch process), also using naturally occurring deposits, while chemically altering them (e.g., concentrated triple superphosphate). Naturally occurring inorganic fertilizers include Chilean sodium nitrate, mine rock phosphate, and limestone.

As used herein, the term "manure" is organic matter used as organic fertilizer in agriculture. Depending on its structure, manure can be divided into liquid manure, semi-liquid manure, stable or solid manure and straw manure. Depending on its origin, manure can be divided into manure derived from animals or plants. Common forms of animal manure include feces, urine, farm slurry (liquid manure) or farmyard manure (FYM) whereas FYM also contains a certain amount of plant material (typically straw), which may have been used as bedding for animals. Animals from which manure can be used comprise horses, cattle, pigs, sheep, chickens, turkeys, rabbits, and guano from seabirds and bats. The application rates of animal manure when used as fertilizer highly depends on the origin (type of animals). Plant manures may derive from any kind of plant whereas the plant may also be grown explicitly for the purpose of plowing them in (e.g., leguminous plants), thus improving the structure and fertility of the soil. Furthermore, plant matter used as manure may include the contents of the rumens of slaughtered ruminants, spent hops (left over from brewing beer) or seaweed.

As used herein, the term "seed" comprises seed of all types, such as, for example, corns, seeds, fruits, tubers, seedlings and similar forms. The seed used can be seed of the useful plants mentioned above, but also the seed of transgenic plants or plants obtained by customary breeding methods.

As used herein, the term "reduce volatility" and the like refers to the volatility of the nitrapyrin salt as compared to that of the nitrapyrin free base. The reduction in volatility can be quantified as described elsewhere herein.

As used herein, the term "organic solvent" refers to a non-aqueous solvent that solvates the nitrapyrin salt to the degree as described elsewhere herein.

As used herein, the term "inhibit urease" and the like refers to the inhibition of the activity of urease. The inhibition can be quantified as described elsewhere herein.

As used herein, "nitrification inhibitor" refers to a property of a compound, such as nitrapyrin, to inhibit oxidation of ammonia to nitrite/nitrate.

Additional definitions may follow below.

II. Compositions

Nitrapyrin complexes with polyanionic species have been prepared. As mentioned above, these complexes can exhibit desirable properties such as a significantly lower vapor pressure, higher loading, and increased chemical stability, all of which generally contribute to an increased performance in the field.

Generally, the nitrapyrin complexes can be used neat or can include an organic solvent, as well as other ingredients to form useful compositions. In some embodiments, the described compositions and formulations contain relatively little to no water. Formulations containing high amounts of water have shown rapid degradation of nitrapyrin and therefore the exposure of nitrapyrin to excessive amounts of water should be minimized. In some embodiments, the amount of water present in neat nitrapyrin complex or in a formulation thereof containing organic solvent is less than about 10%, about 9%, about 8%, about 7%, about 6%, about 5%, about 4%, about 3%, about 2%, about 1%, or is less than 0.5% w/w based on the total weight of the composition. In such composition the chemical stability of the nitrapyrin complex is at least about 50%, about 60%, about 70%, about 80%, about 85%, about 90%, about 91%, about 92%, about 93%, about 94%, about 95%, about 96%, about 97%, about 98%, about 99%, or at least about 99.5%. See for example, Meikle et al. "The hydrolysis and photolysis rates of nitrapyrin in dilute aqueous solution" Arch. Environm. Contain. Toxicol. 7, 149-158 (1978).

A. Nitrapyrin Complexes with Polyanionic Species

Nitrapyrin is a nitrification inhibitor having the structure:

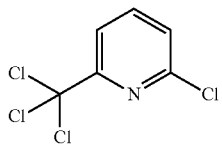 [SMILES: Clc1cccc(C(Cl)(Cl)Cl)n1]

Nitrapyrin is a nitrification inhibitor. It functions to inhibit nitrification within the soil bacteria, *Nitrosomonas*, which act on ammonia by oxidizing ammonium ions to nitrite and/or nitrate. Nitrification inhibition therefore reduces nitrogen emissions from soil.

Complexes of nitrapyrin include those formed with a suitable non-volatile polyanionic species. Polyanionic species include those polyanionic polymers disclosed in WO 2011/016898; WO 2015/031521; US2016/0102027; US2017/0183492; and U.S. Pat. No. 10,059,636, each of which is incorporated by reference in its entirety. Polyanionic species also include non-polymeric molecule having two or more negatively charged groups, Suitable negatively charged groups include, but are not limited to, carboxyl groups, sulfonate groups, phosphonate groups, and mixtures thereof.

Polyanions (polyanionic species) suitable for formation of useful complexes with nitrapyrin have one or more of: a formal charge of −2 or greater (i.e., greater negative charge) in dilute aqueous solution at pH 10, lower vapor pressure when compared to the vapor pressure of nitrapyrin, and/or lower volatility when compared to the volatility of nitrapyrin. In some embodiments, the vapor pressure of the nitrapyrin in the nitrapyrin complex is less than 0.5 mmHg at 20° C. Furthermore, the amount of loading of the nitrapyrin into a formulation has been significantly increased.

In some embodiments, the MW/charge ratio of a polyanion is 50-200, 50-175, 50-150, 50-125, 50-125, 50-110, 50-105, 50-100, 50-95, 50-90, 50-85, 50-80, 50-75, 65-200, 65-175, 65-150, 65-125, 65-125, 65-110, 65-105, 90-115, 90-100, 90-105, 95-120, 95-115, 95-110, 95-105, 50, 55, 60, 65, 70, 75, 80, 85, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 1127, 128, 129, or 130. In some embodiments, the charge ratio (molecular weight/charge) is less than 200, less than 175, less than 150, less than 140, less than 130, less than 125, less than 120, less than 115, less than 110, less than 105, less than 100, less than 95, less than 90, less than 85, less than 80, less than 75, or less than 70. In some embodiments, the MW/charge ratio of a polyanion is greater than 50, greater than 55, greater than 60, greater than 65, greater than 70, greater than 75, greater than 80, greater than 85, greater than 90, greater than 95, or greater than 100.

A number of polyanionic species are suitable for the formation of complexes with nitrapyrin. In some embodiments, the polyanion has a formal charge greater than −2, greater than −3, greater than −4, greater than −5, greater than −6, greater than −7, greater than −8, greater than −9, greater than −10, greater than −15, or greater than −20 at pH 10. As used herein, greater than "−n" means greater negative charge, e.g., −3 has greater negative charge than −2. In some embodiments, the polyanions are polymeric materials having a plurality (two or more) of anionic functional groups, including, but not limited to, carboxylates, sulfonates, and the like.

In some embodiments, the polyanion is a non-polymeric molecule having a plurality (two or more) of anionic functional groups, including, but not limited to, carboxylates, sulfonates, and the like. Non-polymeric polyanions include, but are not limited to, di-, tri-, tetra-, penta-, hexa-, hepta-, octa-, nona-, and deca-carboxyls, di-, tri-, tetra-, penta-, hexa-, hepta-, octa-, nona-, and deca-sulfonates, and di-, tri-, tetra-, penta-, hexa-, hepta-, octa-, nona-, and deca-phosphonates. In some embodiment, a non-polymeric polyanion comprises an aliphatic dibasic acid. In some embodiments, a non-polymeric polyanion comprises aromatic carboxylic acid containing a 2-6 carboxylic acid groups. In some embodiments, a non-polymeric polyanion comprises aliphatic carboxylic acid containing a 2-6 carboxylic acid groups. Exemplary non-polymeric polycarboxylic acids, phosphonates, and aromatic carboxylic acids suitable for forming nitrapyrin complexes include, but are not limited to, malic acid, tartaric acid, etidronic acid, succinic acid, adipic acid, isophthalic acid, aconitic, trimesic, biphenyl-3,3',5,5'-tetracarboxylic acid, furantetracarboxylic acid, sebacic acid, azelaic acid, isoterephtallic acid, isophthallic acid, pyromellitic acid, and mellitic acid.

The amount of nitrapyrin substitution on the polyanion is from about 5% to about 90%, of the available anionic groups, or from about 10% to about 90% of the available anionic groups, or from about 20% to about 90% of the available anionic groups, or from about 30% to about 80% of the available anionic groups, or from about 40% to about 80% of the available anionic groups, or from about 40% to about 75% of the available anionic groups, or from about 50% to about 75% of the available anionic groups. In embodiments, the nitrapyrin complex composition contains from about 50 g/mol anionic species to about 200 g/mol anionic species; or from about 75 g/mol anionic species to about 190 g/mol anionic species, or from about 100 g/mol anionic species to about 180 g/mol anionic species, or about 125 g/mol anionic species to about 175 g/mol anionic species.

In some embodiments, the polyanionic species comprises a polyanionic polymer. In some embodiments, a polyanionic polymer comprises a copolymer containing two or more different repeat units. A copolymer can have two, three, four, or more different repeat units. As used herein, a copolymer contains two or more different repeat units. As used herein, a terpolymer contains three or more different repeat units. As used herein, a tetrapolymer contains four or more different repeat units. A polyanionic polymer can be, but is not limited to, random copolymer, alternating copolymer, periodic copolymer, statistical copolymer, or block copolymer. In some embodiments, the polyanion can be a carboxylated polymer, a sulfonated polymer or an all-sulfonated polymer. An all sulfonated polymer can be, but is not limited to, polystyrene sulfonate. Additionally, the sulfur can be provided by polyanionic species such as ethanedisulfonic acid and 1,3-benzenedisulfonic acid.

In some embodiments, the polyanionic polymers have a high carboxylate content and sulfonate repeat units, which are very soluble in water and biodegradable. In some embodiments, a polyanionic polymer has a single repeating unit, wherein the repeating unit contains a negatively charged group. In some embodiments, a polyanionic polymer comprises a copolymer having two or more repeating units wherein at least one of the repeating units contains a negatively charged group. In some embodiments, a polyanionic polymer comprises a dipolymer having two repeating units wherein at one or both of the repeating units contains a negatively charged group. In some embodiments, a polyanionic polymer comprises a terpolymer having three or more repeating units wherein at least one of the repeating units contains a negatively charged group. In some embodiments, the polyanionic polymers are tetrapolymers having at least four different repeat units distributed along the lengths of the polymer chains, preferably with at least one repeat unit each of maleic, itaconic, and sulfonate repeat units. The repeat units are derived from corresponding monomers used in the synthesis of the polymers. In some embodiments, a polyanionic polymer contains type B, type C, and/or type G repeat units as described in detail below. In some embodiments, a polyanionc polymer contains type B and type C, type B and type G, or type C and type G repeat units as described in detail below. In some embodiments, a polyanionic polymer contains at least one repeat unit from each of three separately defined categories of repeat units, referred to herein as type B, type C, and type G repeat units, and described in detail below. In some embodiments, at least about 90 mole percent of the repeat units therein are selected from the group consisting of type B, C, and G repeat units, and mixtures thereof, the repeat units being randomly located along the polyanionic polymer. In some embodiments, the polyanionic polymer contains no more than about 10 mole percent or no more than 5 mole percent of any of (i) non-carboxylate olefin repeat units, (ii) ether repeat units, (iii) non-sulfonated monocarboxylic repeat units, (iv) non-sulfonated monocarboxylic repeat units, and/or (v) amide-containing repeat units.

"Non-carboxylate" and "non-sulfonated" refers to repeat units having essentially no carboxylate groups or sulfonate groups in the corresponding repeat units.

In some embodiments, a polyanionic polymer comprises a copolymer comprising the structure represented by:

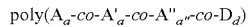

wherein A is a first repeat unit containing a negatively charged group, A' is optional and if present is a second repeat unit containing a negatively charged group, A" is optional and if present is a third repeat unit containing a negatively charged group, and D is optional and if present is an uncharged repeat unit. A polyanionic polymer can contain additional negatively charged repeat units or uncharged repeat units. a is an integer greater than or equal to 1. a', a", and d are integers greater than or equal to zero. The value of (a+a'+a") is greater than or equal to 2.

In some embodiments, the polyanionic polymer comprises a random copolymer having structure represented by:

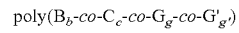

wherein B and C are type B and type C repeat units as described below, G and G' are independently type G repeat units as described below, c is an integer greater than zero and b, g and g' are integers greater than or equal to zero. In some embodiments, the ratio of b:c:(g+g') is about 1-70:1-80:0-65. In some embodiments, the ratio of b:c:(g+g') is about 20-65:15-75:1-35. In some embodiments, the ratio of b:c:(g+g') is about 35-55:20-55:1-25. In some embodiments, the ratio of b+c to g+g' is about 0.5-20:1, about 1-20:1, or about 1-10:1. In some embodiments, the ratio of b:c:g:g' is about 10:90:0:0, about 60:40:0:0, about 50:50:0:0, or about 0:100:0:0. In some embodiments, the ratio of b:c:g:g' is about 45:35:15:5. In some embodiments, the ratio of b:c:g:g' is about 45:50:4:1. In some embodiments, the polymers contain less than 10%, less than 4%, less than 3%, less than 25, less than 1%, less than 0.5%, less than 0.1%, less than 0.05%, less than 0.01% or 0% repeat units that are not B, C, G, or G'.

In some embodiments, the polyanionic polymer comprises a tetrapolymer having repeat units individually and independently selected from the group consisting of type B, type C, and type G repeat units, and mixtures thereof, described in detail below. In some embodiments, a tetrapolymer contains more than four different repeat units. In some embodiments, the additional repeat units are selected from the group consisting of type B, type C, and type G repeat units, and mixtures thereof, as well as other monomers or repeat units not being type B, C, or G repeat units.

In some embodiments, a polyanionic polymer contains at least one repeat unit from each of the B, C, and G types, one other repeat unit selected from the group consisting of type B, type C, and type G repeat units, and optionally other repeat units not selected from type B, type C, and type G repeat units. In some embodiments, a polyanionic polymers comprise a single type B repeat unit, a single type C repeat unit, and two different type G repeat units, or two different type B repeat units, a single type C repeat unit, and one or more different type G repeat units.

In some embodiments, the polyanionic polymers comprise at least 90% or at least 96 mole percent of the repeat units therein selected from the group consisting of type B, C, and G repeat units, and mixtures thereof. In some embodiments, the polyanionic polymers consist of or consist essentially of repeat units selected from the group consisting of type B, C, and G repeat units, and mixtures thereof. In some embodiments, the polyanionic polymers contain <3, <2, <1, <0.5, <0.1, <0.05, <0.01, or 0 mole percent ester groups and/or noncarboxylate olefin groups.

In some embodiments, the total amount of type B repeat units in the polymer is from about 1-70 mole percent, the total amount of type C repeat units in the polymer is from about 1-80 mole percent, and the total amount of type G repeat units in the polymer is from about 0.1-65 mole percent, where the total amount of all of the repeat units in the polymer is taken as 100 mole percent. In some embodiments, the total amount of type B repeat units in the polymer is from about 20-65 mole percent, the total amount of type C repeat units in the polymer is from about 15-75 mole percent, and the total amount of type G repeat units in the polymer is from about 1-35 mole percent, where the total amount of all of the repeat units in the polymer is taken as 100 mole percent.

In some embodiments, the polyanionic polymers have one type B repeat unit, one type C repeat unit, and two different type G repeat units. In some embodiments, the one type B repeat unit is derived from maleic acid, the one type C repeat unit is derived from itaconic acid, and two type G repeat units are respectively derived from methallylsulfonic acid and allylsulfonic acid. In such polymers, the type B repeat unit can be present at a level of from about 35-55 mole percent, the type C repeat unit can present at a level of from about 20-55 mole percent, the type G repeat unit derived from methallylsulfonic acid can present at a level of from about 1-25 mole percent, and the type G repeat unit derived from allylsulfonic acid can be present at a level of from about 1-25 mole percent, where the total amount of all of the repeat units in the polymer is taken as 100 mole percent. In other embodiments, the polyanionic polymers comprise two different type B repeat units, one type C repeat unit, and one type G repeat unit. In some embodiments, the polyanionic polymer contains at least one repeat unit not selected from the group consisting of type B, type C, and type G repeat units.

In some embodiments, the mole ratio of the type B and type C repeat units in combination to the type G repeat units (that is, the mole ratio of (B+C)/G) should be about 0.5-20:1, about 2: 1-20:1, or about 2.5:1-10:1. Still further, the polymers should be essentially free (e.g., less than about 1 mole percent) of alkyloxylates or alkylene oxide (e.g., ethylene oxide)-containing repeat units, and most desirably entirely free thereof.

In some embodiments, the polyanionic polymers have a high percentage of the repeat units thereof bearing at least one anionic group, e.g., at least about 80 mole percent, at least about 90 mole percent, at least about 95 mole percent, or essentially all of the repeat units contain at least one anionic group. It will be appreciated that the B and C repeat units have two anionic groups per repeat unit, whereas the preferred sulfonate repeat units have one anionic group per repeat unit.

In some embodiments, a polyanionic terpolymer comprises a polymer backbone composition range (by mole percent, using the parent monomer names of the corresponding repeat units) of: maleic acid 35-50%; itaconic acid 20-55%; methallylsulfonic acid 1-25%; and allylsulfonic sulfonic acid 1-20%, where the total amount of all of the repeat units in the polymer is taken as 100 mole percent.

The molecular weight of the polymers can be varied, depending upon the desired properties. The molecular weight distribution for any of the polyanionic polymers can be measured by size exclusion chromatography. In some embodiments, a polyanionic polymer has a molecule weight greater than 118, greater than 150, greater than 200, greater than 300, greater than 400, or greater than 500 Da. In some embodiments, the polyanionic polymers have a molecular weight of about 100-50,000 Da. In some embodiments, the polyanionic polymers have a molecular weight of about 100-5000 Da, about 200-5000 Da, about 400-5000 Da, or about 1000-5000 Da. In some embodiments, at least 90% of the finished polyanionic polymer is at or above a molecular weight of about 100, 200, 400, or 1000 measured by size exclusion chromatography in 0.1 M sodium nitrate solution via refractive index detection at 35° C. using polyethylene glycol standards. Other methods of determining polymer molecular known in the art can also be employed.

Type B Repeat Units

Type B repeat units can be selected from the group consisting of repeat units derived from substituted and unsubstituted monomers of maleic acid and/or maleic anhydride, fumaric acid mesaconic acid, mixtures of the foregoing, and any isomers, esters, acid chlorides, and partial or complete salts of any of the foregoing. Type B repeat units may be substituted with one or more $C_1$-$C_6$ straight or branched chain alkyl groups substantially free of ring structures and halo atoms, wherein substantially free means no more than about 5 mole percent or no more than about 1 mole percent of either ring structures or halo substituent. Substituents are normally bound to one of the carbons of a carbon-carbon double bond of the monomer(s) employed.

Those skilled in the art will appreciate the usefulness of in situ conversion of acid anhydrides to acids in a reaction vessel just before or even during a reaction. However, it is also understood that when corresponding esters (e.g., maleic or citraconic esters) are used as monomers during the initial polymerization, this should be followed by hydrolysis (acid or base) of pendant ester groups to generate a final carboxylated polymer substantially free of ester groups.

Type C Repeat Units

Type C repeat units can be selected from the group consisting of repeat units derived from substituted or unsubstituted monomers of itaconic acid or itaconic anhydride, and any isomers, esters, and the partial or complete salts of any of the foregoing and mixtures of any of the foregoing. Type C repeat units may be substituted with one or more $C_1$-$C_6$ straight or branched chain alkyl groups substantially free of ring structures and halo atoms.

The itaconic acid monomer used to form type C repeat unit has one carboxyl group, which is not directly attached to the unsaturated carbon-carbon double bond used in the polymerization of the monomer. In some embodiments, a type C repeat unit has one carboxyl group directly bound to the polymer backbone, and another carboxyl group spaced by a carbon atom from the polymer backbone. The definitions and discussion relating to "substituted," "salt," and useful salt-forming cations (metals, amines, and mixtures thereof) with respect to the type C repeat units, are the same as those set forth for the type B repeat units.

In some embodiments, the type C repeat unit is an unsubstituted itaconic acid or itaconic anhydride, either alone or in various mixtures. If itaconic anhydride is used as a starting monomer, it is normally useful to convert the itaconic anhydride monomer to the acid form in a reaction vessel just before or even during the polymerization reaction. Any remaining ester groups in the polymer are normally hydrolyzed, so that the final carboxylated polymer is substantially free of ester groups.

Type G Repeat Units

Type G repeat units can be selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing. Type G repeat units may be substituted with one or more $C_1$-$C_6$ straight or branched chain alkyl groups substantially free of ring structures and halo atoms.

In some embodiments, type G repeat units can be selected from the group consisting of $C_1$-$C_8$ straight or branched chain alkenyl sulfonates, substituted forms thereof, and any isomers or salts of any of the foregoing; especially preferred are alkenyl sulfonates selected from the group consisting of vinyl, allyl, and methallylsulfonic acids or salts.

In some embodiments, the type G repeat units are derived from vinylsulfonic acid, allylsulfonic acid, and methallylsulfonic acid, either alone or in various mixtures. It has also been found that alkali metal salts of these acids are also highly useful as monomers. In this connection, it was unexpectedly discovered that during polymerization reactions yielding the novel polymers disclosed herein, the presence of mixtures of alkali metal salts of these monomers with acid forms thereof does not inhibit completion of the polymerization reaction. By the same token, mixtures of monomers of maleic acid, itaconic acid, sodium allyl sulfonate, and sodium methallyl sulfonate do not inhibit the polymerization reaction.

Syntheses of BC and BCG polymers are described in WO 2015/031521, incorporated herein by reference in its entirety.

A.1. Class I polymers

Class IA Polymers

Class IA polymers contain both carboxylate and sulfonate functional groups, but are not the tetra- and higher order polymers of Class I. For example, terpolymers of maleic, itaconic, and allylsulfonic repeat units will function as the polyanionic polymer component of the compositions. The Class IA polymers thus are normally homopolymers, copolymers, and terpolymers, advantageously including repeat units individually and independently selected from the group consisting of type B, type C, and type G repeat units, without the need for any additional repeat units. Such polymers can be synthesized in any known fashion, and can also be produced using the previously described Class I polymer synthesis.

Class IA polymers preferably have the same molecular weight ranges and the other specific parameters (e.g., pH and polymer solids loading) previously described in connection with the Class I polymers, and maybe converted to partial or complete salts using the same techniques described with reference to the Class I polymers. Class IA polymers are most advantageously synthesized using the techniques described above in connection with the Class I polymers.

A.2. Class II Polymers

Broadly speaking, the polyanionic polymers of this class are of the type disclosed in U.S. Pat. No. 8,043,995, which is incorporated herein by reference in its entirety. The polymers include repeat units derived from at least two different monomers individually and respectively taken from the group consisting of what have been denominated for ease of reference as B' and C' monomers; alternately, the polymers may be formed as homopolymers or copolymers from recurring C' monomers. The repeat units may be randomly distributed throughout the polymer chains.

In detail, repeat unit B' is of the general formula

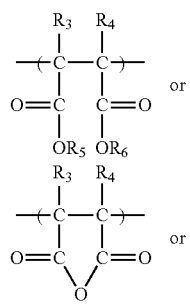

or and repeat unit C is of the general formula

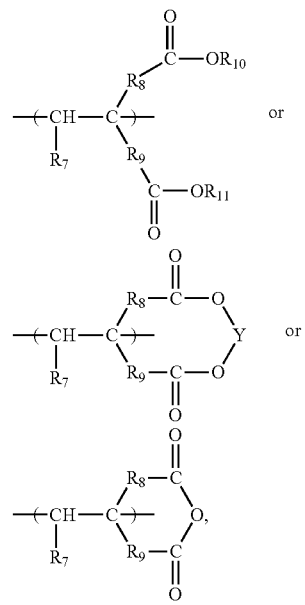

wherein each $R_7$ is individually and respectively selected from the group consisting of H, OH, $C_1$-$C_{30}$ straight, branched chain and cyclic alkyl or aryl groups, $C_1$-$C_{30}$ straight, branched chain and cyclic alkyl or aryl formate ($C_0$), acetate ($C_1$), propionate ($C_2$), butyrate ($C_3$), etc. up to $C_{30}$ based ester groups, R'$CO_2$ groups, OR' groups and COOX groups, wherein R' is selected from the group consisting of $C_1$-$C_{30}$ straight, branched chain and cyclic alkyl or aryl groups and X is selected from the group consisting of H, the alkali metals, $NH_4$ and the $C_1$-$C_4$ alkyl ammonium groups, $R_3$ and $R_4$ are individually and respectively selected from the group consisting of H, $C_1$-$C_{30}$ straight, branched chain and cyclic alkyl or aryl groups, $R_5$, $R_6$, $R_{10}$ and $R_{11}$ are individually and respectively selected from the group consisting of H, the alkali metals, $NH_4$ and the $C_1$-$C_4$ alkyl ammonium groups, Y is selected from the group consisting of Fe, Mn, Mg, Zn, Cu, Ni, Co, Mo, V, W, the alkali metals, the alkaline earth metals, polyatomic cations containing any of the foregoing (e.g., $VO^{+2}$), amines, and mixtures thereof; and $R_8$ and $R_9$ are individually and respectively selected from the group consisting of nothing (i.e., the groups are non-existent), $CH_2$, $C_2H_4$, and $C_3H_6$.

As can be appreciated, the Class II polymers typically have different types and sequences of repeat units. For example, a Class II polymer comprising B' and C' repeat units may include all three forms of B' repeat units and all three forms of C' repeat units. However, for reasons of cost and ease of synthesis, the most useful Class II polymers are made up of B' and C' repeat units. In the case of the Class II polymers made up principally of B' and C' repeat units, $R_5$, $R_6$, $R_{10}$, and $R_{11}$ are individually and respectively selected from the group consisting of H, the alkali metals, $NH_4$, and the $C_1$-$C_4$ alkyl ammonium groups. This particular Class II polymer is sometimes referred to as a butanedioic methylenesuccinic acid copolymer and can include various salts and derivatives thereof.

The Class II polymers may have a wide range of repeat unit concentrations in the polymer. For example, Class II polymers having varying ratios of B':C' (e.g., 10:90, 60:40, 50:50 and even 0:100) are contemplated and embraced by the presently disclosed subject matter. Such polymers would be produced by varying monomer amounts in the reaction mixture from which the final product is eventually produced and the B' and C' type repeat units may be arranged in the polymer backbone in random order or in an alternating pattern.

The Class II polymers may have a wide variety of molecular weights, ranging for example from 500-5,000,000, depending chiefly upon the desired end use. Additionally, n can range from about 1-10,000 and more preferably from about 1-5,000.

Class II polymers can be synthesized using dicarboxylic acid monomers, as well as precursors and derivatives thereof. For example, polymers containing mono and dicarboxylic acid repeat units with vinyl ester repeat units and vinyl alcohol repeat units are contemplated; however, polymers principally comprised of dicarboxylic acid repeat units are preferred (e.g., at least about 85%, and more preferably at least about 93%, of the repeat units are of this character). Class II polymers may be readily complexed with salt-forming cations using conventional methods and reactants.

In some embodiments, the Class II polymers is composed of maleic and itaconic B' and C' repeat units and have the generalized formula:

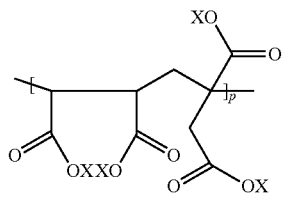

where X is either H or another salt-forming cation, depending upon the level of salt formation.

In a specific example of the synthesis of a maleic-itaconic Class II polymer, acetone (803 g), maleic anhydride (140 g), itaconic acid (185 g) and benzoyl peroxide (11 g) were stirred together under inert gas in a reactor. The reactor provided included a suitably sized cylindrical jacketed glass reactor with mechanical agitator, a contents temperature measurement device in contact with the contents of the reactor, an inert gas inlet, and a removable reflux condenser. This mixture was heated by circulating heated oil in the reactor jacket and stirred vigorously at an internal temperature of about 65-70° C. This reaction was carried out over a period of about 5 hours. At this point, the contents of the reaction vessel were poured into 300 g water with vigorous mixing. This gave a clear solution. The solution was subjected to distillation at reduced pressure to drive off excess solvent and water. After sufficient solvent and water have been removed, the solid product of the reaction precipitates from the concentrated solution, and is recovered. The solids are subsequently dried in vacuo.

In some embodiments, the polyanionic polymer has repeat unit molar composition of 45 mole percent maleic repeat units, 50 mole percent itaconic repeat units, 4 mole percent methallylsulfonate repeat units, and 1 mole percent allylsulfonate repeat units. This polymer is referred to herein as the "T5" polymer.

In some embodiments the polyanionic polymer comprises: 45% maleic repeat units, 35% itaconic repeat units, 15% methallylsulfonate repeat units, and 5% allylsulfonate repeat units.

In some embodiments, the polyanionic polymers comprises: 45% maleic repeat units, 50% itaconic repeat units, 4% methallylsulfonate repeat units, and 1% allylsulfonate repeat units.

In some embodiments, a nitrapyrin complex can be formed with two or more different polyanionic polymers.

In embodiments, nitrapyrin can be present as a mixture of the complex and the free form. The ratio of complex to free form can be from 1000:1 to 0.1:1 such that the compositions can reduce the volatilization losses of nitrapyrin to atmosphere by at least 10% as compared to an identical composition lacking the complex described herein. Accordingly, the compositions described herein can simultaneously comprise the complex and the free form so long as the volatilization losses are reduced as described elsewhere herein.

B. Organic Solvents

In some embodiments, the solvent is an organic solvent. In some embodiments, the solvent is a polar organic solvent. In some embodiments, the polar organic solvent is EPA approved. EPA approved solvents are those that are approved for food and non-food use and found in the electronic code of federal regulations, for example in Title 40, Chapter I, Subchapter E, Part 180. EPA approved solvent include, but are not limited to, the solvents listed in Table 1.

TABLE 1

| EPA approved solvents | |
|---|---|
| 1,3-Propanediol (CAS Reg. No. 504-63-2) | Isopropyl-3-hydroxybutyrate (CAS Reg. No. 54074-94-1) |
| 2-Ethylhexanol | Kerosene, U.S.P. reagent |
| 2-methyl-1,3-propanediol (CAS Reg. No. 2163-42-0) | Lactic acid |
| 2-Methyl-2,4-pentanediol | Lactic acid, 2-ethylhexyl ester (CAS Reg. No. 6283-86-9) |
| Acetic anhydride | Lactic acid, n-propyl ester, (S); (CAS Reg. No. 53651-69-7) |
| Acetone (CAS Reg. No. 67-64-1) | Mesityl oxide |
| Ammonium hydroxide | Methyl 5-(dimethylamino)-2-methyl-5-oxopentanoate (1174627-68-9) |
| Amyl acetate | Methyl alcohol |
| Benzyl acetate (CAS Reg. No. 140-11-4) | Methyl esters of fatty acids derived from edible fats and oils |

TABLE 1-continued

EPA approved solvents

| | |
|---|---|
| C10-11 rich aromatic hydrocarbons (CAS Reg. No. 64742-94-5) | Methyl isobutyl ketone |
| C11-12 rich aromatic hydrocarbons (CAS Reg. No. 64742-94-5) | Methyl isobutyrate (CAS Reg. No. 547-63-7) |
| C9 rich aromatic hydrocarbons (CAS Reg. No. 64742-95-6) | Methyl n-amyl ketone (CAS Reg. No. 110-43-0) |
| Choline chloride (CAS Reg. No. 67-48-1) | Mineral oil |
| Cod liver oil | Morpholine 4-$C_{6-12}$ Acyl Derivatives (CAS Reg. No. 887947-29-7) |
| Cyclohexane | n-Butanol (CAS Reg. No. 71-36-3) |
| Cyclohexanone | n-Butyl benzoate (CAS Reg. No.136-60-7) |
| Decanamide, N,N-dimethyl (CAS Reg. No. 14433-76-2) | n-Butyl-3-hydroxybutyrate (CAS Reg. No. 53605-94-0) |
| Diethylene Glycol (CAS No. 111-46-6) | n-Decyl alcohol (CAS Reg. No. 112-30-1) |
| Diethylene glycol mono butyl ether (CAS Reg. No. 112-34-5) | n-Hexyl alcohol (CAS Reg. No. 111-27-3) |
| Diethylene Glycol MonoEthyl Ether (CAS Reg. No. 111-90-0) | N-Methylpyrrolidone (CAS Reg. No. 872-504) |
| Diethylphthalate | n-Octyl alcohol (CAS Reg. No. 111-87-5) |
| Diisopropyl adipate (CAS Reg. No. 6938-94-9) | n-Propanol |
| Dimethyl adipate (CAS no. 627-93-0) | Octanamide, N,N-dimethyl (CAS Reg. No. 1118-92-9) |
| Dimethyl glutarate (CAS no. 1119-40-0) | Oxo-decyl acetate (CAS reg. No. 108419-33-6) |
| Dimethyl succinate (CAS no. 106-65-0) | Oxo-heptyl acetate (CAS Reg. No. 90438-79-2) |
| Dimethyl sulfoxide (CAS No. 67-68-5) | Oxo-hexyl acetate (CAS Reg. No. 88230-35-7) |
| Di-n-butyl carbonate (CAS Reg. No. 542-52-9) | Oxo-nonyl acetate (CAS Reg. No. 108419-34-7) |
| Dipropylene glycol | Oxo-octyl acetate (CAS Reg. No. 108419-32-5) |
| Distillates, (Fishcher-Tropsch), heavy, $C_{18}$-$C_{50}$, branched, cyclic and linear (CAS Reg. No. 848301-69-9) | Oxo-tridecyl acetate (CAS Reg. No. 108419-35-8) |
| d-Limonene (CAS Reg. No. 5989-27-5) | Petroleum hydrocarbons, light odorless conforming to 21 CFR 172.884 |
| Edible fats and oils. | Phenol |
| Ethyl acetate | Propanoic acid, 2-methyl-, monoester with 2,2,4-trimethyl-1,3-pentanediol (CAS Reg. No. 25265-77-4) |
| Ethyl alcohol | Propylene glycol |
| Ethyl esters of fatty acids derived from edible fats and oils | Propylene glycol monomethyl ether (CAS No. 107-98-2) |
| Ethylene glycol (CAS Reg. No. 107-21-1) | Soybean oil-derived fatty acids |
| Glycerol mono-, di-, and triacetate | Tall oil fatty acid (CAS Reg. No. 61790-12-3) |
| Hydrochloric acid | Tetraethylene glycol (CAS Reg. No. 112-60-7) |
| Isobornyl acetate | Toluenesulfonic acid |
| Isobutyl Acetate (CAS Reg. No. 110-19-0) | Triacetin (glyceryl triacetate) |
| Isobutyl isobutyrate (CAS Reg. No. 97-85-8) | Xylene |
| Isobutyric Acid (CAS Reg. No. 79-31-2) | γ-Butyrolactone |
| Isopropyl myristate (CAS Reg. No. 110-27-0) | |

In some embodiments, the organic solvent is relatively free of water. In some embodiments, the organic solvent contains less than about 10% w/w, about 9% w/w, about 8% w/w, about 7% w/w, about 6% w/w, about 5% w/w, about 4% w/w, about 3% w/w, about 2% w/w, about 1% w/w, about 0.9% w/w, about 0.8% w/w, about 0.7% w/w, about 0.6% w/w, about 0.5% w/w, about 0.4% w/w, about 0.3% w/w, or less than about 0.1% w/w of water based on the total weight of the solvent.

In some embodiments, the organic solvent is a liquid at 20° C. In other embodiments, the organic solvent is a solid at 20° C.

In some embodiments, the solvent is a sulfone. A sulfone solvent can be, but is not limited to, sulfolane, methyl sulfolane (3-methyl sulfolane), and dimethylsulfone. Sulfones, in contrast to sulfoxide and ester solvents were found to possess better solvent properties and improved handling safety characteristics. In some embodiments, the sulfone is a liquid at 20° C. In some embodiments, the sulfone is a solid at 20° C.

In some embodiments, the solvent is an ether-polyol. An ether-polyol solvent can be, but is not limited to, polyethylene glycols, polypropylene glycols, polyalkylene glycols, and related compounds. In some embodiments, a polypropylene glycol has three terminal alcohols. Exemplary polypropylene glycols having three terminal alcohols, known as propoxylated glycerol, include Dow PT250 and Dow PT700. In some embodiments, ether-polyol comprises a polyethylene or a polypropylene glycol in the molecular weight range of between about 200 and about 10,000 Da. It has been found that nitrapyrin complex compositions containing ether polyols are more suitable for formation of higher solids and/or actives content than previously described compositions containing esters. In some embodiments, the ether-polyol is a liquid at 20° C. In some embodiments, the ether-polyol is a solid at 20° C.

In some embodiments, an organic solvent can be, but is not limited to, aromatic solvent such as but not limited to, alkyl substituted benzene, xylene, propylbenzene, mixed naphthalene and alkyl naphthalene, and mineral oils; kerosene; dialkyl amides of fatty acids, including but not limited to, dimethylamides of fatty acids, dimethyl amide of caprylic acid; chlorinated aliphatic and aromatic hydrocarbons, including but not limited to, 1,1,1-trichloroethane, chlorobenzene, esters of glycol derivatives, n-butyl, ethyl, or methyl ether of diethyleneglycol and acetate of the methyl ether of dipropylene glycol; ketones, including but not limited to, isophorone and trimethylcyclohexanone (dihydroisophorone); and acetate, including but not limited to, hexyl and heptyl acetate.

In some embodiments, an organic solvent can be, but is not limited to, aromatic 100 (CAS No: 64742-95-6), aromatic 200 (CAS No. 64742-94-5), sulfone, glycol, polyglycol, dipropylene glycol, Dow PT250, Dow PT700, PT250, triethylene glycol, tripropylene glycol, propylene carbonate, triacetin, dialkylamides of saturated monocarboxylic acids containing between 3 and 20 carbon atoms, such as Agnique AMD810, Rhodiasolv ADMA10, Rhodiasolv and ADMA810, dialkylamides of alpha-hydroxycarboxylic acids containing between 2 and 10 carbon atoms, such as Agnique AMD3L, Rhodiasolv Polarclean, or mixtures thereof. In some embodiments, the organic solvent is selected from Agnique AMD810, Agnique AMD3L, Rhodiasolv ADMA10, Rhodiasol ADMA810, Rhodiasol Polarclean, and mixtures thereof.

In some embodiments, nitrapyrin complexes can be formulated with two different solvent types. Nitrapyrin complexes formulated in two different solvent types can exhibit high solvation, relative lack of volatility, and suitable environmental and toxicological profiles. The two difference solvent types can be selected from two different sulfones, two difference ether-polyols, or a sulfone and an ether-polyol. In some embodiments, solvency of the nitrapyrin in solution/solvent at 20° C. is greater than 15% w/w (nitrapyrin to total weight), for example from about 15 to about 22% w/w, or about 17% to about 21% w/w, or greater than 16% w/w, greater than 17% w/w, greater than 18% w/w, greater than 19% w/w, greater than 20% w/w, greater than 21% w/w, greater than 22% w/w, greater than 23% w/w, greater than 24% w/w, or greater than 25% w/w greater than 26% w/w, greater than 27% w/w, greater than 28% w/w, greater than 29% w/w, greater than 30% w/w, greater than 35% w/w, greater than 40% w/w, or greater than 45% w/w.

The solvent can be present in the composition at an amount from 0.1% w/v to about 99.9% w/v. In some embodiments, the amount of solvent will be minimized as the amount of nitrapyrin complex of a polyanionic polymer is maximized. In some embodiments, the amount of solvent is less than 80% w/v, less than 79% w/v, less than 78% w/v, less than 77% w/v, less than 76% w/v, less than 75% w/v, less than 74% w/v, less than 73% w/v, less than 72% w/v, less than 71% w/v, less than 70% w/v, less than 65% w/v, less than 60% w/v, or less than 55% w/v. In embodiments, the amount of solvent is from 55% w/v to about 98% w/v; or from about 60% w/v to about 97% w/v; or from about 61% w/v to about 95% w/v; or from about 62% w/v to about 90% w/v; or from about 63% w/v to about 85% w/v; or from about 64% w/v to about 80% w/v.

The composition comprises nitrapyrin in the form of a complex. Advantageously, nitrapyrin complexes with polyanions have been found to provide excellent loading heretofore not disclosed. Advantages of the highly concentrated compositions include lower cost of shipping and ease of handling. In embodiments, the compositions comprise nitrapyrin in a range from about 20% to about 50% by wt. In embodiments, the compositions comprise nitrapyrin in a range from about 21% to about 49% by wt. In embodiments, the compositions comprise nitrapyrin in a range from about 22% to about 48% by wt. In embodiments, the compositions comprise nitrapyrin in a range from about 23% to about 47% by wt. In embodiments, the compositions comprise nitrapyrin in a range from about 24% to about 46% by wt. In embodiments, the compositions comprise nitrapyrin in a range from about 25% to about 45% by wt. In embodiments, the compositions comprise nitrapyrin in a range from about 26% to about 40% by wt. In embodiments, the compositions comprise nitrapyrin in a range from about 27% to about 35% by wt. In embodiments, the compositions comprise nitrapyrin in a range from about 28% to about 32% by wt. In embodiments, the compositions comprise nitrapyrin in an amount of about 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% by wt.

In some embodiments, compositions containing nitrapyrin complexes are disclosed. The nitrapyrin complexes are more readily dissolved in appropriate solvents when compared to nitrapyrin alone or with prior art formulations. The described nitrapyrin complexes can form solutions that are greater than or equal to 25% nitrapyrin by weight. Suitable solvents include, but are not limited to, aromatic 100 (CAS No: 64742-95-6), aromatic 200 (CAS No. 64742-94-5), sulfones, and glycols.

In embodiments, the nitrapyrin complex with a polyanion and compositions comprising the complexes reduce volatility of the nitrapyrin by about 5% to about 40% relative to untreated nitrapyrin. In embodiments, the nitrapyrin complex with a polyanion and compositions comprising the complexes reduce volatility of the nitrapyrin by about 8% to about 35% relative to untreated nitrapyrin. In embodiments, the nitrapyrin complex with a polyanion and compositions comprising the complexes reduce volatility of the nitrapyrin by about 10% to about 30% relative to untreated nitrapyrin. In embodiments, the nitrapyrin complex with a polyanion and compositions comprising the complexes reduce volatility of the nitrapyrin by about 5, 6, 7, 8, 9, 10, 11, 12, 13, 14, 15, 16, 17, 18, 19, 20, 21, 22, 23, 24, 25, 26, 27, 28, or 29%.

In embodiments, the composition comprises the following solvent-nitrapyrin acid complex combinations: one or more of malic acid, tartaric acid, etidronic acid, succinic acid, adipic acid, sebacic acid, isophthalic acid, maleic-acrylic copolymer, BC and/or T5, and one or more of dipropylene glycol, PT700, PT250, triethylene glycol, tripropylene glycol, propylene carbonate, triacetin, Agnique AMD810, Agnique AMD3L, Rhodiasolv ADMA10, Rhodiasolv ADMA810 and/or Rhodiasolv Polarclean. In some embodiments, the composition comprises the following solvent-nitrapyrin acid complex combinations: one or more of malic acid, tartaric acid, etidronic acid, succinic acid, and/or adipic acid, and one or more of Agnique AMD810, Agnique AMD3L, Rhodiasolv ADMA10, Rhodiasolv ADMA810 and/or Rhodiasolv Polarclean. In some embodiments, the composition comprises the following solvent-nitrapyrin acid complex combinations: one or more of sebacic acid, and/or T5 and one or more of Agnique AMD3L, Rhodiasolv ADMA810 and/or Rhodiasolv Polarclean.

III. Agricultural Products

Any of the described nitrapyrin complexes can be combined with one or more other ingredients, selected from the group consisting of fertilizer, agriculturally active compounds, seed, compounds having urease inhibition activity, nitrification inhibition activity, pesticides, herbicides, insecticides, fungicides, miticides and the like.

In some embodiments, the described nitrapyrin complexes may be mixed with the fertilizer products, applied as a surface coating to the fertilizer products, or otherwise thoroughly mixed with the fertilizer products. In some embodiments, in such combined fertilizer/nitrapyrin complex composition, the fertilizer is in the form of particles having an average diameter of from about powder size (less than about 0.001 cm) to about 10 mm, more preferably from about 0.1 mm to about 5 mm, and still more preferably from about 0.15 mm to about 3 mm. The nitrapyrin can be present in such combined products at a level of about 0.001 g to about 20 g per 100 g fertilizer, about 0.01 to 7 g per 100 g fertilizer, about 0.08 g to about 5 g per 100 g fertilizer, or about 0.09 g to about 2 g per 100 g fertilizer. In the case of the combined fertilizer/nitrapyrin complex products, the combined product can be applied at a level so that the amount of nitrapyrin complex applied is about 10-150 g per acre of soil, about 30-125 g per acre, or about 40-120 g per acre of soil. The combined products can likewise be applied as liquid dispersions or as dry granulated products, at the discretion of the user. When nitrapyrin complexes are used as a coating, the nitrapyrin complex can comprise between about 0.005% and about 15% by weight of the coated fertilizer product, about 0.01% and about 10% by weight of the coated fertilizer product, about 0.05% and about 2% by weight of the coated fertilizer product or about 0.5% and about 1% by weight of the coated fertilizer product.

A. Fertilizers

In some embodiments, the agricultural product is a fertilizer. The fertilizer can be a solid fertilizer, such as, but not limited to a granular fertilizer, and the nitrapyrin complex can be applied to the fertilizer as a liquid dispersion. The fertilizer can be in liquid form, and the nitrapyrin complex can be mixed with the liquid fertilizer. The fertilizers can be selected from the group consisting of starter fertilizers, phosphate-based fertilizers, fertilizers containing nitrogen, fertilizers containing phosphorus, fertilizers containing potassium, fertilizers containing calcium, fertilizers containing magnesium, fertilizers containing boron, fertilizers containing chlorine, fertilizers containing zinc, fertilizers containing manganese, fertilizers containing copper, fertilizers containing urea and ammonium nitrite and/or fertilizers containing molybdenum materials. In some embodiments, the fertilizer is or contains urea, and/or ammonia, including anhydrous ammonia fertilizer. In some embodiments, the fertilizer comprises plant-available nitrogen, phosphorous, potassium, sulfur, calcium, magnesium or micronutrients. In some embodiments, the fertilizer is solid, granular, a fluid suspension, a gas, or a solutionized fertilizer. In some embodiments, the fertilizer comprises a micronutrient. A micronutrient is an essential element required by a plant in small quantities. In some embodiments, the fertilizer comprises a metal ion selected from the group consisting of: Fe, Mn, Mg, Zn, Cu, Ni, Co, Mo, V and Ca. In some embodiments, the fertilizer comprises gypsum, Kieserite Group member, potassium product, potassium magnesium sulfate, elemental sulfur, or potassium magnesium sulfate. Such fertilizers may be granular, liquid, gaseous, or mixtures (e.g., suspensions of solid fertilizer particles in liquid material).

In some embodiments, the nitrapyrin complex is combined with any suitable liquid or dry fertilizer for application to fields and/or crops.

The described nitrapyrin complexes, or compositions thereof, can be applied with the application of a fertilizer. The nitrapyrin complexes can be applied prior to, subsequent to, or simultaneously with the application of fertilizers.

Nitrapyrin complex-containing fertilizer compositions can be applied in any manner which will benefit the crop of interest. In some embodiments, a fertilizer composition is are applied to growth mediums in a band or row application. In some embodiment, the compositions are applied to or throughout the growth medium prior to seeding or transplanting the desired crop plant. In some embodiment, the compositions can be applied to the root zone of growing plants.

B. Seed

In some embodiments are described agricultural seeds coated with one or more of the described nitrapyrin complexes. The nitrapyrin complex can be present in the seed product at a level of from about 0.001-10%, about 0.004%-2%, about 0.01% to about 1%, or from about 0.1% to about 1% by weight (or no more than about 10%, about 9%, about 8%, about 7% about 6%, about 5%, about 4%, about 3%, about 2%, about 1%, about 0.5%, about 0.1%, about 0.01% or no more than 0.001%), based upon the total weight of the coated seed product. A seed can be, but is not limited to, wheat, barley, oat, triticale, rye, rice, maize, soya bean, cotton, or oilseed rape.

C. Other

In some embodiments are described urease inhibiting compounds, nitrification inhibiting compounds, pesticides, herbicides, insecticides, fungicides, and/or miticides in combination with one or more of the described nitrapyrin complexes. As used herein "pesticide" refers to any agent with pesticidal activity (e.g., herbicides, insecticides, fungicides) and is preferably selected from the group consisting of insecticides, herbicides, and mixtures thereof, but normally excluding materials which assertedly have plant-fertilizing effect, for example sodium borate and zinc compounds such as zinc oxide, zinc sulfate, and zinc chloride. For an unlimited list of pesticides see "Farm Chemicals Handbook 2000, 2004" (Meister Publishing Co, Willoughby, Ohio), which is hereby incorporated by reference in its entirety.

Exemplary herbicides include, but are not limited to acetochlor, alachlor, aminopyralid, atrazine, benoxacor, bromoxynil, carfentrazone, chlorsulfuron, clodinafop, clopyralid, dicamba, diclofop-methyl, dimethenamid, fenoxaprop, flucarbazone, flufenacet, flumetsulam, flumiclorac, fluroxypyr, glufosinate-ammonium, glyphosate, halosulfuron-methyl, imazamethabenz, imazamox, imazapyr, imazaquin, imazethapyr, isoxaflutole, quinclorac, MCPA, MCP amine, MCP ester, mefenoxam, mesotrione, metolachlor, s-metolachlor, metribuzin, metsulfuron methyl, nicosulfuron, paraquat, pendimethalin, picloram, primisulfuron, propoxycarbazone, prosulfuron, pyraflufen ethyl, rimsulfuron, simazine, sulfosulfuron, thifensulfuron, topramezone, tralkoxydim, triallate, triasulfuron, tribenuron, triclopyr, trifluralin, 2,4-D, 2,4-D amine, 2,4-D ester and the like.

Exemplary insecticides include, but are not limited to 1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuformin, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cyclopro- thrin, cyenopyrafen, cyflumetofen, cyfluthrin, cyhalothrin, cyhexatin, cypermethrin, cyphenothrin, cyromazine, cythioate, d-limonene, dazomet, DBCP. DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfiram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfiram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos.

Exemplary fungicides include, but are not be limited to, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulfide, benalaxyl, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, bixafen, blasticidin-S, Bordeaux mixture, boric acid, boscalid, bridged diphenyl fungicides, bromuconazole, bupirimate, Burgundy mixture, buthiobate, sec-butylamine, calcium polysulfide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroform, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper(II) carbonate, basic, copper fungicides, copper hydroxide, copper naphthenate, copper oleate, copper oxychloride, copper(II) sulfate, copper sulfate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, diniconazole-M, dinitrophenol fungicides, dinobuton, dinocap, dinocap-4, dinocap-6, dinocton, dinopenton, dinosulfon, dinoterbon, diphenylamine, dipyrithione, disulfiram, ditalimfos, dithianon, dithiocarbamate fungicides, DNOC, dodemorph, dodicin, dodine, donatodine, drazoxolon, edifenphos, epoxiconazole, etaconazole, etem, ethaboxam, ethirimol, ethoxyquin, ethylene oxide, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, Fluconazole, fludioxonil, flumetover, flumorph, fluopicolide, fluoroimide, fluotrimazole, fluoxastrobin, fluquinconazole, flusilazole, flusulfamide, flutolanil, flutriafol, fluxapyroxad, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isopropyl alcohol, isoprothiolane, isovaledione, isopyrazam, kasugamycin, ketoconazole, kresoxim-methyl, Lime sulfur (lime sulphur), mancopper, mancozeb, maneb, mebenil, mecarbinzid, mepanipyrim, mepronil, mercuric chloride (obsolete), mercuric oxide (obsolete), mercurous chloride (obsolete), metalaxyl, metalaxyl-M (a.k.a. Mefenoxam), metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulfonanilide, nabam, natamycin, nystatin, β-nitrostyrene, nitrothal-isopropyl, nuarimol, OCH, octhilinone, ofurace, oprodione, organomercury fungicides, organophosphorus fungicides, organotin fungicides (obsolete), orthophenyl phenol, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, Phosphite, phthalide, phthalimide fungicides, picoxystrobin, piperalin, polycarbamate, polymeric dithiocarbamate fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinomethionate, quinone fungicides, quinoxaline fungicides, quinoxyfen, quintozene, rabenzazole, salicylanilide, silthiofam, silver, simeconazole, sodium azide, sodium bicarbonate[2][3], sodium orthophenylphenoxide, sodium pentachlorophenoxide, sodium polysulfide, spiroxamine, streptomycin, strobilurin fungicides, sulfonanilide fungicides, sulfur, sulfuryl fluoride, sultropen, TCMTB, tebuconazole, tecloftalam, tecnazene, tecoram, tetraconazole, thiabendazole, thiadifluor, thiazole fungicides, thicyofen, thifluzamide, thymol, triforine, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, Undecylenic acid, uniconazole, uniconazole-P, urea fungicides, validamycin, valinamide fungicides, vinclozolin, voriconazole, zarilamid, zinc naphthenate, zineb, ziram, and/or zoxamide.

In some embodiments, the composition of the presently disclosed subject matter is a pesticide/nitrapyrin-containing composition comprising a pesticide and a nitrapyrin complex. In some embodiments, the pesticide is an herbicide, insecticide or a combination thereof.

In some embodiments, the composition of the presently disclosed subject matter is a fungicide/nitrapyrin-containing composition comprising a fungicide and a nitrapyrin complex.

The amount of nitrapyrin complex in the pesticide/nitrapyrin containing composition and/or fungicide/nitrapyrin-containing composition can vary. In some embodiments, the amount of nitrapyrin complex is present at a level of from about 0.05-10% by weight (more preferably from about 0.1%-4% by weight, and most preferably from about 0.2-2% by weight) based upon the total weight of the pesticide/nitrapyrin containing composition or fungicide/nitrapyrin-containing composition taken as 100% by weight.

Exemplary classes of miticides include, but are not be limited to botanical acaricides, bridged diphenyl acaricides, carbamate acaricides, oxime carbamate acaricides, carbazate acaricides, dinitrophenol acaricides, formamidine acaricides, isoxaline acaricides, macrocyclic lactone acaricides, avermectin acaricides, milbemycin acaricides, milbemycin acaricides, mite growth regulators, organochlorine acaricides, organophosphate acaricides, organothiophosphate acaricides, phosphonate acaricides, phosphoarmidothiolate acaricies, organitin acaricides, phenylsulfonamide acaricides, pyrazolecarboxamide acaricdes, pyrethroid ether acaricide, quaternary ammonium acaricides, oyrethroid ester acaricides, pyrrole acaricides, quinoxaline acaricides, methoxyacrylate strobilurin acaricides, teronic acid acaricides, thiasolidine acaricides, thiocarbamate acaricides, thiourea acaricides, and unclassified acaricides. Examples of miticides for these classes include, but are not limited to, to botanical acaricides—carvacrol, sanguinarine; bridged diphenyl acaricides—azobenzene, benzoximate, benzyl, benzoate, bromopropylate, chlorbenside, chlorfenethol, chlorfenson, chlorfensulphide, chlorobenzilate, chloropropylate, cyflumetofen, DDT, dicofol, diphenyl, sulfone, dofenapyn, fenson, fentrifanil, fluorbenside, genit, hexachlorophene, phenproxide, proclonol, tetradifon, tetrasul; carbamate acaricides—benomyl, carbanolate, carbaryl, carbofuran, methiocarb, metolcarb, promacyl, propoxur; oxime carbamate acaricides—aldicarb, butocarboxim, oxamyl, thiocarboxime, thiofanox; carbazate acaricides—bifenazate; dinitrophenol acaricides—binapacryl, dinex, dinobuton, dinocap, dinocap-4, dinocap-6, dinocton, dinopenton, dinosulfon, dinoterbon, DNOC; formamidine acaricides—amitraz, chlordimeform, chloromebuform, formetanate, formparanate, medimeform, semiamitraz; isoxazoline acaricides—afoxolaner, fluralaner, lotilaner, sarolaner; macrocyclic lactone acaricides—tetranactin; avermectin acaricides—abamectin, doramectin, eprinomectin, ivermectin, selamectin; milbemycin acaricides—milbemectin, milbemycin, oxime, moxidectin; mite growth regulators—clofentezine, cyromazine, diflovidazin, dofenapyn, fluazuron, flubenzimine, flucycloxuron, flufenoxuron, hexythiazox; organochlorine acaricides—bromociclen, camphechlor, DDT, dienochlor, endosulfan, lindane; organophosphate acaricides—chlorfenvinphos, crotoxyphos, dichlorvos, heptenophos, mevinphos, monocrotophos, naled, TEPP, tetrachlorvinphos; organothiophosphate acaricides—amidithion, amiton, azinphos-ethyl, azinphosmethyl, azothoate, benoxafos, bromophos, bromophosethyl, carbophenothion, chlorpyrifos, chlorthiophos, coumaphos, cyanthoate, demeton, demeton-O, demeton-S, demeton-methyl, demeton-O-methyl, demeton-S-methyl, demeton-S-methylsulphon, dialifos, diazinon, dimethoate, dioxathion, disulfoton, endothion, ethion, ethoate-methyl, formothion, malathion, mecarbam, methacrifos, omethoate, oxydeprofos, oxydisulfoton, parathion, phenkapton, phorate, phosalone, phosmet, phostin, phoxim, pirimiphos-methyl, prothidathion, prothoate, pyrimitate, quinalphos, quintiofos, sophamide, sulfotep, thiometon, triazophos, trifenofos, vamidothion; phosphonate acaricides—trichlorfon; phosphoramidothioate acaricides—isocarbophos, methamidophos, propetamphos; phosphorodiamide acaricides—dimefox, mipafox, schradan; organotin acaricides—azocyclotin, cyhexatin, fenbutatin, oxide, phostin; phenylsulfamide acaricides—dichlofluanid; phthalimide acaricides—dialifos, phosmet; pyrazole acaricides—cyenopyrafen, fenpyroximate; phenylpyrazole acaricides—aceto-prole, fipronil, vaniliprole; pyrazolecarboxamide acaricides—pyflubumide, tebufenpyrad; pyrethroid ester acaricides—acrinathrin, bifenthrin, brofluthrinate, cyhalothrin, cypermethrin, alpha-cypermethrin, fenpropathrin, fenvalerate, flucythrinate, flumethrin, fluvalinate, tau-fluvalinate, permethrin; pyrethroid ether acaricides—halfenprox; pyrimidinamine acaricides—pyrimidifen; pyrrole acaricides—chlorfenapyr; quaternary ammonium acaricides—sanguinarine; quinoxaline acaricides—chinomethionat, thioquinox; methoxyacrylate strobilurin acaricides—bifujunzhi, fluacrypyrim, flufenoxystrobin, pyriminostrobin; sulfite ester acaricides—aramite, propargite; tetronic acid acaricides—spirodiclofen; tetrazine acaricides, clofentezine, diflovidazin; thiazolidine acaricides—flubenzimine, hexythiazox; thiocarbamate acaricides—fenothiocarb; thiourea acaricides—chloromethiuron, diafenthiuron; unclassified acaricides—acequinocyl, acynonapyr, amidoflumet, arsenous, oxide, clenpirin, closantel, crotamiton, cycloprate, cymiazole, disulfiram, etoxazole, fenazaflor, fenazaquin, fluenetil, mesulfen, MNAF, nifluridide, nikkomycins, pyridaben, sulfiram, sulfluramid, sulfur, thuringiensin, triarathene.

In some embodiments, a miticide can also be selected from abamectin, acephate, acequinocyl, acetamiprid, aldicarb, allethrin, aluminum phosphide, aminocarb, amitraz, azadiractin, azinphos-ethyl, azinphos-methyl, *Bacillus thuringiensis*, bendiocarb, beta-cyfluthrin, bifenazate, bifenthrin, bomyl, buprofezin, calcium cyanide, carbaryl, carbofuran, carbon disulfide, carbon tetrachloride, chlorfenvinphos, chlorobenzilate, chloropicrin, chlorpyrifos, clofentezine, chlorfenapyr, clothianidin, coumaphos, crotoxyphos, crotoxyphos+dichlorvos, cryolite, cyfluthrin, cyromazine, cypermethrin, deet, deltamethrin, demeton, diazinon, dichlofenthion, dichloropropene, dichlorvos, dicofol, dicrotophos, dieldrin, dienochlor, diflubenzuron, dikar (fungicide+miticide), dimethoate, dinocap, dinotefuran, dioxathion, disulfoton, emamectin benzoate, endosulfan, endrin, esfenvalerate, ethion, ethoprop, ethylene dibromide, ethylene dichloride, etoxazole, famphur, fenitrothion, fenoxycarb, fenpropathrin, fenpyroximate, fensulfothion, fenthion, fenvalerate, flonicamid, flucythrinate, fluvalinate, fonofos, formetanate hydrochloride, gamma-cyhalothrin, halofenozide, hexakis, hexythiazox, hydramethylnon, hydrated lime, indoxacarb, imidacloprid, kerosene, kinoprene, lambda-cyhalothrin, lead arsenate, lindane, malathion, mephosfolan, metaldehyde, metam-sodium, methamidophos, methidathion, methiocarb, methomyl, methoprene, methoxychlor, methoxyfenozide, methyl bromide, methyl parathion, mevinphos, mexacarbate, Milky Disease Spores, naled, naphthalene, nicotine sulfate, novaluron, oxamyl, oxydemeton-methyl, oxythioquinox, para-dichlorobenzene, parathion, PCP, permethrin, petroleum oils, phorate, phosalone, phosfolan, phosmet, phosphamidon, phoxim, piperonyl butoxide, pirimicarb, pirimiphos-methyl, profenofos, propargite, propetamphos, propoxur, pymetrozine, pyrethroids—synthetic: see allethrin, permethrin, fenvalerate, resmethrin, pyrethrum, pyridaben, pyriproxyfen, resmethrin, rotenone, s-methoprene, soap, pesticidal, sodium fluoride, spinosad, spiromesifen, sulfotep, sulprofos, temephos, terbufos, tetrachlorvinphos, tetrachlorvinphos+dichlorvos, tetradifon, thiamethoxam, thiodicarb, toxaphene, tralomethrin, trimethacarb, and tebufenozide.

IV. Methods

In some embodiments, the nitrapyrin complexes are used directly. In other embodiments, the nitrapyrin complexes are formulated in ways to make their use convenient in the context of productive agriculture. The nitrapyrin complexes used in these methods include the nitrapyrin complexes as described above. In addition, the nitrapyrin complexes used in these methods also include nitrapyrin complexes wherein nitrapyrin is complexed with hydrochloric acid and phosphoric acid. The nitrapyrin complexes can be used in methods such as:

A. Methods of Improving Plant Growth and/or Fertilizing Soil
B. Methods of Inhibiting Nitrification or Ammonia Release or Evolution
C. Methods of Reducing Nitrapyrin Volatilization
D. Methods of Improving Soil Conditions
E. Methods of Preparing a Nitrapyrin Complexes A. Methods for improving plant growth comprise contacting a nitrapyrin complex or a composition containing a nitrapyrin complex as disclosed herein with soil. In some embodiments, the nitrapyrin complex or composition is applied to the soil prior to emergence of a planted crop. In some embodiments, the nitrapyrin complex is applied to the soil adjacent to the plant and/or at the base of the plant and/or in the root zone of the plant.

Methods for improving plant growth can also be achieved by applying a nitrapyrin complex or a composition containing a nitrapyrin complex as a seed coating to a seed in the form of a liquid dispersion which upon drying forms a dry residue. In these embodiments, seed coating provides the nitrapyrin complex in close proximity to the seed when planted so that the nitrapyrin complex can exert its beneficial effects in the environment where it is most needed. That is, the nitrapyrin complex provides an environment conducive to enhanced plant growth in the area where the effects can be localized around the desired plant. In the case of seeds, the coating containing the nitrapyrin complex provides an enhanced opportunity for seed germination, subsequent plant growth, and an increase in plant nutrient availability.

B. Methods for inhibiting/reducing nitrification or ammonia release or evolution in an affected area comprises applying a nitrapyrin complex or composition containing a nitrapyrin complex to the affected area. The affected area may be soil adjacent to a plant, a field, a pasture, a livestock or poultry confinement facility, pet litter, a manure collection zone, an upright walls forming an enclosure, or a roof substantially covering the area, and in such cases the nitrapyrin complex may be applied directly to the manure in the collection zone. The nitrapyrin complex is preferably applied at a level from about 0.005-3 gallons per ton of manure, in the form of an aqueous dispersion having a pH from about 1-5.

C. Methods of reducing nitrapyrin volatilization comprise complexation of nitrapyrin with polyanions thereby forming a nitrapyrin complex. Nitrapyrin complexes are less volatile compared to the nitrapyrin free base. In some embodiments, the nitrapyrin complexes reduce volatility by about 5% to about 40%, about 8% to about 35%, or about 10% to about 30% (or by about 5, 6, 7, 8, 9, 10, 11, 12, 13, 14, 15, 16, 17, 18, 19, 20, 21, 22, 23, 24, 25, 26, 27, 28, or 29%) relative to untreated nitrapyrin.

D. Methods for improving soil conditions selected from the group consisting of nitrification processes, urease activities, and combinations thereof, comprising the step of applying to soil an effective amount of a described nitrapyrin complex or composition containing a nitrapyrin complex. In some embodiments, the nitrapyrin complex is mixed with an ammoniacal solid, liquid, or gaseous fertilizer, and especially solid fertilizers; in the latter case, the nitrapyrin complex is applied to the surface of the fertilizer as an aqueous dispersion followed by drying, so that the nitrapyrin complex is present on the solid fertilizer as a dried residue. The nitrapyrin complex is generally applied at a level of from about 0.01-10% by weight, based upon the total weight of the nitrapyrin complex/fertilizer product taken as 100% by weight. Where the fertilizer is an aqueous liquid fertilizer, the nitrapyrin complex is added thereto with mixing. The nitrapyrin complex is preferably in aqueous dispersion and have a pH of up to about 3.

E. Methods of preparing a nitrapyrin complexes, comprises contacting nitrapyrin with one or more solvents to form a first mixture, contacting the first mixture with a polyanion to form a complex of nitrapyrin and a polyanion.

In some embodiments, the methods A, B, and D above comprise contacting a desired area with a nitrapyrin complex at a rate of about 100 g to about 120 g per acre of the nitrapyrin salt. The nitrapyrin complex can, in some embodiments, be in solution at an amount of about 0.5 lbs. to about 4 lbs. per U.S. gallon, or from about 1 lb. to about 3 lbs/per U.S. gallon, or about 2 lbs. per U.S. gallon. In some embodiments, the method includes contacting the desired area at a rate of about 0.5 to about 4 qt/A, or about 1 to about 2 qt/A.

Particular embodiments of the subject matter described herein include:

1. A nitrapyrin complex comprising a nitrapyrin complexed with a polyanion.

2. The nitrapyrin complex of embodiment 1, wherein the polyanion has a MW/charge ratio of 65-200.

3. The nitrapyrin complex of any above embodiment, wherein the polyanion comprises a non-polymeric polyanion.

4. The nitrapyrin complex of any above embodiment, wherein the non-polymeric polyanion comprises a di-, tri-, tetra-, penta-, hexa-, hepta-, octa-, nona-, or deca-carboxyl, a di-, tri-, tetra-, penta-, hexa-, hepta-, octa-, nona-, or deca-sulfonate, or a di-, tri-, tetra-, penta-, hexa-, hepta-, octa-, nona-, or deca-phosphonate.

5. The nitrapyrin complex of any above embodiment, wherein the non-polymeric polyanion comprises a di-, tri-, tetra-, penta-, hexa-, hepta-carboxyl.

6. The nitrapyrin complex of any above embodiment, wherein the non-polymeric polyanion comprises an aliphatic carboxylic acid or an aromatic carboxyl.

7. The nitrapyrin complex of any above embodiment, wherein the non-polymeric polyanion is selected from the list consisting of: malic acid, tartaric acid, etidronic acid, succinic acid, adipic acid, isophthalic acid, aconitic, trimesic, biphenyl-3,3',5,5'-tetracarboxylic acid, furantetracarboxylic acid, sebacic acid, azelaic acid, isoterephtalic acid, pyromellitic acid, and mellitic acid.

8. The nitrapyrin complex of embodiment 1 or 2, wherein the polyanion comprises a polyanionic polymer.

9. The nitrapyrin complex of embodiment 8, wherein the polyanionic polymer contains at least 80 mole percent repeat units containing at least one anionic group.

10. The nitrapyrin complex of embodiment 8 or 9, wherein the polyanionic polymer has a net formal charge less than −5 in dilute aqueous solution at pH 10.

11. The nitrapyrin complex of embodiment 8 or 9, wherein the polyanionic polymer has a net formal charge less than −10 in dilute aqueous solution at pH 10.

12. The nitrapyrin complex of embodiment 8, 9, 10 or 11, wherein the polyanionic polymer has a lower vapor pressure as compared to the vapor pressure of nitrapyrin.

13. The nitrapyrin complex of embodiment 8, 9, 10, 11 or 12, wherein the vapor pressure of the polyanionic polymer is less than 0.5 mm Hg vapor pressure at 20° C.

14. The nitrapyrin complex of embodiment 8, 9, 10, 11, 12 or 13, wherein the polyanionic polymer is a random copolymer.

15. The nitrapyrin complex of embodiment 8, 9, 10, 11, 12 or 13, wherein the polyanionic polymer is a terpolymer.

16. The nitrapyrin complex of embodiment 8, 9, 10, 11, 12, 13, 14, or 15, wherein the polyanion has a net formal charge less than −2 in dilute aqueous solution at pH10.

17. The nitrapyrin complex of embodiment 8, 9, 10, 11, 12, 13, 14, 15, or 16, wherein the polyanionic polymer is a tetrapolymer.

18. The nitrapyrin complex of any above embodiment, wherein the complex is a salt.

19. The nitrapyrin complex of any above embodiment, wherein the complex is a chelate.

20. The nitrapyrin complex of any above embodiment, wherein the complex is a complex.

21. The nitrapyrin complex of any above embodiment, where the polyanionic polymer comprises a random copolymer having at least two repeat units including at least one each of type B and type C repeat unites, and optionally one or more different type G repeat units, wherein a) the type B repeat units are independently selected from the group consisting of repeat units derived from substituted and unsubstituted monomers of maleic acid, maleic anhydride, fumaric acid, mesaconic acid, mixtures of the foregoing, and any isomers, esters, acid chlorides, and partial or complete salts of any of the foregoing, wherein type B repeat units may be substituted with one or more $C_1$-$C_6$ straight or branched chain alkyl groups substantially free of ring structures and halo atoms, and wherein the salts have salt-forming cations selected from the group consisting of metals, amines, and mixtures thereof, b) the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more $C_1$-$C_6$ straight or branched chain alkyl groups substantially free of ring structures and halo atoms, and wherein the salts have salt-forming cations selected from the group consisting of metals, amines, and mixtures thereof, and c) the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more $C_1$-$C_6$ straight or branched chain alkyl groups substantially free of ring structures and halo atoms, and wherein the salts of the type G repeat units have salt-forming cations selected from the group consisting of metals, amines, and mixtures thereof, and wherein at least about 90 mole percent of the repeat units therein are selected from the group consisting of type B, C, and G repeat units, and mixtures thereof, and, wherein the polyanionic polymer contains no more than about 10 mole percent of any of (i) non-carboxylate olefin repeat units, (ii) ether repeat units, and (iii) non-sulfonated monocarboxylic repeat units.

22. The nitrapyrin complex of embodiment 21, wherein the polyanionic polymer consists of one type B repeat unit derived from maleic acid, one type C repeat unit derived from itaconic acid, and two type G repeat units respectively derived from methallylsulfonic acid and allylsulfonic acid.

23. The nitrapyrin complex of embodiment 21 or 22, wherein the polyanionic polymer has a repeat unit molar composition of 1-70 mole percent type B repeat units, 1-80 mole percent type C repeat units, and 0.1-65 mole percent type G repeat units.

24. The nitrapyrin complex of embodiment 21 or 22, wherein the polyanionic polymer has a repeat unit molar composition of 20-65 mole percent type B repeat units, 15-75 mole percent type C repeat units, and 1-35 mole percent type G repeat units.

25. The nitrapyrin complex of embodiment 21 or 22, wherein the polyanionic polymer has a repeat unit molar composition of 35-55 mole percent type B repeat units, 20-55 mole percent type C repeat units, and 1-25 mole percent methallylsulfonic repeat units, and 1-20 mole percent allylsulfonic repeat units.

26. The nitrapyrin complex of embodiment 21 or 22, wherein the polyanionic polymer has a repeat unit molar composition of 45 mole percent maleic repeat units, 50 mole percent itaconic repeat units, 4 mole percent methallylsulfonic repeat units, and 1 mole percent allylsulfonic repeat units.

27. The nitrapyrin complex of embodiment 21 or 22, wherein the polyanionic polymer has a repeat unit molar composition of 45 mole percent maleic repeat units, 35 mole percent itaconic repeat units, 15 mole percent methallylsulfonate repeat units, and 5 mole percent allylsulfonate repeat units.

28. The nitrapyrin complex of embodiment 21, wherein the polyanionic polymer is a copolymer consisting of B type and C type repeat units.

29. The nitrapyrin complex of embodiment 21, wherein the polyanionic polymer is a copolymer consisting of maleic and itaconic repeat units.

30. The nitrapyrin complex of embodiment 21, wherein the polyanionic polymer is a homopolymer having B type or C type repeat units.

31. The nitrapyrin complex of embodiment 1, 2, 8, 9, 10, 11, 12, 13, 14, 15, 16, 17, 18, 19, 20, 21, 22, 23, 24, 25, 26, 27, 28, 29 or 30, wherein the polyanionic polymer has an average molecular weight of about 100-50,000 Da.

32. The nitrapyrin complex of embodiment 1, 2, 8, 9, 10, 11, 12, 13, 14, 15, 16, 17, 18, 19, 20, 21, 22, 23, 24, 25, 26, 27, 28, 29, 30 or 31, wherein the polyanionic polymer has an average molecular weight of about 100-5000 Da.

33. A composition comprising an agricultural product and a nitrapyrin complex with a polyanion.

34. The composition of embodiment 33, wherein the agricultural product is selected from the group consisting of fertilizer, seed, urease inhibiting compound, nitrification inhibiting compound, pesticide, herbicide, insecticide, fungicide, and/or miticide.

35. The composition of embodiment 33 or 34, wherein the agricultural product is a fertilizer.

36. The composition of embodiments 34 or 35, wherein the fertilizer is a liquid, solid, granular, fluid suspension, gas, or solutionized fertilizer.

37. The composition of embodiment 34, 35 or 36, wherein the fertilizer is a solid or granular fertilizer.

38. The composition of embodiment 34, 35, 36 or 37, wherein the nitrapyrin complex is provided as a coating on the granular fertilizer.

39. The composition of embodiment 34, 35, 36, 37 or 38, wherein nitrapyrin complex is applied to the fertilizer as a liquid dispersion.

40. The composition of embodiment 34, 35, 36, 37, 38 or 39, wherein the nitrapyrin complex is applied to the surface of the fertilizer.

41. The composition of embodiment 34, 35, 36, 37, 38, 39 or 40, wherein the fertilizer is in liquid form and the nitrapyrin complex is mixed with the liquid fertilizer.

42. The composition of embodiment 33, 34, 35, 36, 37, 38, 39, 40 or 41, wherein the nitrapyrin complex is present at a level of about 0.001 to about 20 g per 100 g of the fertilizer.

43. The composition of embodiment 33, 34, 35, 36, 37, 38, 39, 40, 41 or 42, wherein the nitrapyrin complex is present at a level of about 0.01-10% w/w.

44. The composition of embodiment 33, 34, 35, 36, 37, 38, 39, 40, 41, 42 or 43, wherein the nitrapyrin complex is present at a level of about 0.05-2% w/w.

45. The composition of embodiment 34, 35, 36, 37, 38, 39, 40, 41, 42, 43 or 44, wherein the fertilizer is selected from the group consists of: starter fertilizers, phosphate-based fertilizers, fertilizers containing nitrogen, fertilizers containing phosphorus, fertilizers containing potassium, fertilizers containing calcium, fertilizers containing magnesium, fertilizers containing boron, fertilizers containing zinc, fertilizers containing manganese, fertilizers containing copper, fertilizers containing molybdenum materials, and mixture thereof.

46. The composition of embodiment 34, 35, 36, 37, 38, 39, 40, 41, 42, 43, 44 or 45, wherein the fertilizer comprises urea and ammonium nitrite.

47. The composition of embodiments 33, 34, 35, 36, 37, 38, 39, 40, 41, 42, 43, 44, 45 or 46, wherein the fertilizer comprises anhydrous ammonia.

48. The composition of embodiments 33, 34, 35, 36, 37, 38, 39, 40, 41, 42, 43, 44, 45, 46 or 47, wherein the fertilizer is or contains urea.

49. The composition of embodiment 33, 34, 35, 36, 37, 38, 39, 40, 41, 42, 43, 44, 45, 46, 47 or 48, wherein the fertilizer contains one or more of gypsum, Kieserite Group member, potassium product, potassium magnesium sulfate, elemental sulfur, potassium magnesium sulfate.

50. The composition of embodiment 33, wherein the agricultural product is a seed that is coated with the nitrapyrin complex to form a coated seed product.

51. The composition of embodiment 50, wherein the nitrapyrin complex is present at a level of from about 0.001-10% by weight, based upon the total weight of the coated seed product.

52. The composition of embodiment 33, 34, 35, 36, 37, 38, 39, 40, 41, 42, 43, 44, 45, 46, 47, 48 or 49, wherein said nitrapyrin complex is initially applied to a solid as an aqueous dispersion followed by drying thereof, so that the nitrapyrin complex is in the form of a dried residue.

53. The composition of embodiment 33, 34, 35, 36, 37, 38, 39, 40, 41, 42, 43, 44, 45, 46, 47, 48, 49, 50, 51 or 52, wherein the nitrapyrin complex comprises a complex of nitrapyrin with a polyanion.

54. The composition of embodiment 33, 34, 35, 36, 37, 38, 39, 40, 41, 42, 43, 44, 45, 46, 47, 48, 49, 50, 51 or 52, wherein the nitrapyrin complex comprises a nitrapyrin complex according to any one of embodiments 1-32.

55. The composition of any above embodiment, wherein the composition reduces evolution of atmosphere ammonia when contacted with an area subject to evolution of ammonia.

56. The composition of any above embodiment, wherein the composition reduces evolution is from about 10% to about 30% lower compared to nitrapyrin free base.

57. A composition comprising the nitrapyrin complex of any one of embodiments 1-32 and an organic solvent.

58. The composition of any above embodiment wherein the organic solvent is an EPA approved solvent selected from the group listed in Table 1.

59. The composition of embodiment 57 or 58, wherein the organic solvent is polar.

60. The composition of embodiment 57, 58, or 59, wherein the solvent is selected from the group consisting of: aromatic solvent, alkyl substituted benzene, xylene, propylbenzene, mixed naphthalene and alkyl naphthalene, mineral oil, kerosene, dialkyl amide of fatty acid, dimethylamide of fatty acid, dimethyl amide of caprylic acid, chlorinated aliphatic hydrocarbon, aromatic hydrocarbon, 1,1,1-trichloroethane, chlorobenzene, ester of glycol derivative, n-butyl ether of diethyleneglycol, ethyl ether of diethyleneglycol, methyl ether of diethyleneglycol, acetate of the methyl ether of dipropylene glycol, ketone, isophorone, trimethylcyclohexanone (dihydroisophorone), acetate, hexyl acetate, and heptyl acetate.

61. The composition of embodiment 57, 58 or 59 wherein the solvent is selected from the group consisting of: aromatic 100 (CAS No: 64742-95-6), aromatic 200 (CAS No. 64742-94-5), sulfones, glycols, polyglycol, dipropylene glycol, Dow PT250, Dow PT700, PT250, triethylene glycol, tripropylene glycol, propylene carbonate, triacetin, Agnique AMD810, Agnique AMD3L, Rhodiasolv ADMA10, Rhodiasolv ADMA810, Rhodiasolv Polarclean, and mixtures thereof.

62. The composition of embodiment 61, wherein the sulfone is a sulfolane, methyl sulfolane, or dimethylsulfone.

63. The composition of embodiment 61, wherein the glycol is an ether-polyol.

64. The composition of embodiment 57 or 58, wherein the organic solvent is a ether-polyol selected from polyethylene glycol, polypropylene glycol, polyalkylene glycol, Dow PT250, and Dow PT700.

65. The composition of any above embodiment, wherein the nitrapyrin is present in an amount greater than or equal to 22% by weight.

66. The composition of embodiment 57, 58, 59, 60, 61, 62, 63, 64 or 65, wherein the organic solvent is a liquid at 20° C.

67. The composition of embodiment 57, 58, 59, 60, 61, 62, 63, 64 or 65, wherein the organic solvent is a solid at 20° C.

68. The composition of any above embodiment, wherein said concentration of nitrapyrin is from about 20% to about 50% wt/wt.

69. The composition of any above embodiment, wherein said concentration of nitrapyrin is from about 22% to about 48% wt.

70. The composition of any above embodiment, wherein said concentration of nitrapyrin is from about 25% to about 45% wt.

71. The composition of any above embodiment, wherein the composition exhibits lower nitrapyrin volatility compared to nitrapyrin formulations that do not contain the nitrapyrin salt.

72. A composition comprising:
a nitrapyrin complex with a polyanionic polymer, wherein said polymer comprises:
recurring polymeric subunits each made up of at least two different moieties individually and respectively taken from the group consisting of B and C moieties, wherein moiety B is a dicarboxylic moiety of the general formula

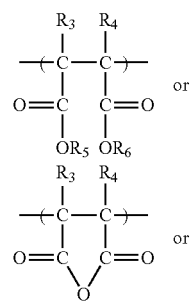

-continued

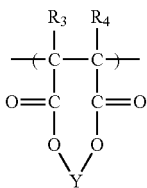

and moiety C is a dicarboxylic moiety of the general formula

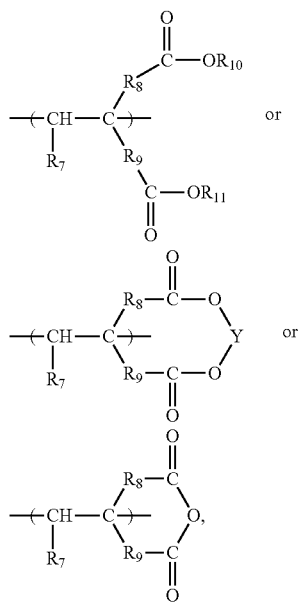

wherein each $R_7$ is individually and respectively selected from the group consisting of H, OH, $C_1$-$C_{30}$ straight, branched chain and cyclic alkyl or aryl groups, $C_1$-$C_{30}$ straight, branched chain and cyclic alkyl or aryl based ester groups, $R^1CO_2$ groups, $OR'$ groups and COOS groups, wherein R' is selected from the group consisting of $C_1$-$C_{30}$ straight, branched chain and cyclic alkyl or aryl groups and X is selected from the group consisting of H, the alkali metals, $NH_4$ and the $C_1$-$C_4$ alkyl ammonium groups, $R_3$ and are individually and respectively selected from the group consisting of H, $C_1$-$C_{30}$ straight, branched chain and cyclic alkyl or aryl groups, $R_5$, $R_6$, $R_{10}$ and $R_{11}$ are individually and respectively selected from the group consisting of H, the alkali metals, $NH_4$ and the $C_1$-$C_4$ alkyl ammonium groups, Y is selected from the group consisting of Fe, Mn, Mg, Zn, Cu, Ni, Co, Mo, V and Ca, and $R_8$ and $R_9$ are individually and respectively selected from the group consisting of nothing (i.e., the groups are nonexistent), $CH_2$, $C_2H_4$, and $C_3H_6$, each of said moieties having or being modified to have a total of two COO groups therein, all of the moieties making up the polymer being dicarboxylic moieties; and an organic solvent.

73. The composition of embodiment 72, wherein said organic solvent is selected from the group consisting of: aromatic 100 (CAS No: 64742-95-6), aromatic 200 (CAS No. 64742-94-5), sulfones, glycols, polyglycol, dipropylene glycol, Dow PT250, Dow PT700, triethylene glycol, tripropylene glycol, propylene carbonate, triacetin, Agnique AMD810, Agnique AMD3L, Rhodiasolv ADMA10, Rhodiasolv ADMA810, Rhodiasolv Polarclean, and mixtures thereof 74. The composition of embodiment 72 or 73, wherein the solvent is selected from the group consisting of glycols, polyglycol, dipropylene glycol, triethylene glycol, and tripropylene glycol.

75. The composition of embodiment 72 or 73, wherein the solvent is sulfolane.

76. The composition of embodiment 72, 73, 74 or 75, wherein said recurring polymeric subunits are made up of B and C moieties, wherein $R_3$ and $R_4$ are each H, and $R_5$ and $R_6$ are Na.

77. The composition of embodiment 72, 73, 74, 75 or 76, wherein $R_4$ is individually and respectively selected from the group consisting of H, OH and $C_1$-$C_4$ straight and branched chain alkyl groups, $R_5$, $R_6$ and X are individually and respectively selected from the group consisting of the alkali metals.

78. The composition of embodiment 72, 73, 74, 75, 76 or 77, said polymer being complexed with a metal ion.

79. The composition of embodiment 72, 73, 74, 75, 76, 77 or 78, said metal ion being selected from the group consisting of Fe, Mn, Mg, Zn, Cu, Ni, Co, Mo, V and Ca.

80. The composition of embodiment 72, 73, 74, 75, 76, 77, 78 or 79 wherein the nitrapyrin complex has lower volatility as compared to nitrapyrin free base.

81. The composition of embodiment 72, 73, 74, 75, 76, 77, 78, 79 or 80, further comprising a fertilizer.

82. The composition of embodiment 81, wherein the fertilizer comprises plant-available nitrogen, phosphorous, potassium, sulfur, calcium, magnesium or micronutrients.

83. The composition of embodiment 81 or 82, wherein the fertilizer is or contains urea, and/or ammonia.

84. A method of fertilizing soil comprising the step of contacting a nitrapyrin complex with a polyanion or a composition comprising a nitrapyrin complex with a polyanion to the soil.

85. A method of improving plant growth and/or health comprising contacting a nitrapyrin complex or a composition comprising a nitrapyrin complex to the soil.

86. The method of embodiments 84 and/or 85, wherein the nitrapyrin complex or a composition containing a nitrapyrin complex is applied to the soil prior to emergence of a planted crop.

87. The method of embodiment 86, wherein the nitrapyrin complex is a complex or composition thereof according to any one of embodiments 1-82.

88. The method embodiment 84, 85 or 87, wherein the nitrapyrin complex or a composition containing a nitrapyrin complex is applied to soil adjacent to a plant, at the base of the plant, or in the root zone of the plant.

89. The method of embodiment 85, 86, 87 or 88, wherein the plant or crop is selected from the group consisting of: cereal, wheat, barley, oat, triticale, rye, rice, maize, soya beans, potato, vegetable, peanuts, cotton, oilseed rape and fruit plant.

90. A method of reducing atmospheric ammonia comprising contacting a nitrapyrin complex or a composition containing a nitrapyrin complex with a polyanion of any above embodiment in an area subject to evolution of ammonia.

91. A method of reducing nitrification in an area comprising contacting a nitrapyrin complex of a polyanion or a composition containing a nitrapyrin complex of a polyanion of any above embodiment in an area subject to nitrification.

92. The method of embodiment 91, wherein reducing nitrification reduces ammonia emissions.

93. The method of embodiment 90 or 91, wherein the area comprises soil, field, pasture, livestock or poultry confinement facility, manure collection zone, upright walls forming an enclosure, and a roof substantially covering the area, pet litter, or manure within the area.
94. The method of claim 93, wherein nitrapyrin complex is applied to the manure within the area in the form of a liquid dispersion at a level from about 0.005-3 gallons per ton of manure.
95. A method of inhibiting a soil condition selected from the group consisting of nitrification processes, urease activities, and combinations thereof, comprising contacting an effective amount of a nitrapyrin complex with a polyanion of any above embodiment with the soil.
96. The method of embodiment 95, further comprising mixing the nitrapyrin complex with an ammoniacal solid, liquid, or gaseous fertilizer prior to the contacting step.
97. The method of embodiment 96, wherein the fertilizer is a solid and the nitrapyrin complex is applied as an aqueous dispersion followed by drying to produce a solid fertilizer coated with dry residue of nitrapyrin complex.
98. The method of embodiments 96 or 97, wherein the nitrapyrin complex is applied at a level of from about 0.01-10% by weight, based upon the total weight of the nitrapyrin complex/fertilizer product taken as 100%.
99. A method of reducing nitrapyrin volatilization by complexing nitrapyrin free base with a polyanionic species.
100. The method of embodiment 99, wherein volatilization is reduced by about 10% to about 30% compared to nitrapyrin free base.
101. The method of embodiment 85, 86, 87, 88, 89, 90, 91, 92, 93, 94, 95, 96, 97 or 98 wherein the contacting comprises contacting at a rate of about 100 g to about 120 g per acre of the nitrapyrin salt.
102. A method of preparing the composition of claim 1, comprising
contacting nitrapyrin with one or more solvents to form a first mixture,
contacting the first mixture with a polyanion to form a complex of nitrapyrin and a polyanion.

EXAMPLES

It should be understood that the following Examples are provided by way of illustration only and nothing therein should be taken as a limiting.

Example 1. Decreased Volatility of Nitrapyrin/Polyanionic Polymer Salts

Three materials were placed on a heated balance at 100° C. and had their weights observed every minute for 10 minutes, as a percent of original weight. The materials were:
1. pure nitrapyrin,
2. 25% w/w solution of nitrapyrin in sulfolane, and
3. solution of 25% nitrapyrin salt with equimolar (on acid basis) amount of maleic-itaconic copolymer, also in sulfolane (nitrapyrin/polyanionic polymer salt).

The weight loss data in Tables 2-3 show that polyanionic polymer salt of nitrapyrin exhibited significantly decrease rate of nitrapyrin loss as compared to free nitrapyrin, both as a solution and as free nitrapyrin. The data show a 10-30% reduction in volatilization of the nitrapyrin when used in the salt form as compared to untreated. Therefore, the disclosed nitrapyrin salts substantially reduce the volatilization of nitrapyrin.

TABLE 2

Nitrapyrin volatilization from 25% w/w actives sulfolane solution formulations at 100° C.

| Experiment time, min. | nitrapyrin solution (no polymer) | % per minute loss rate untreated | % of original nitrapyrin lost | nitrapyrin polyanionic polymer salt solution | % per minute loss rate treated | % original nitrapyrin lost | % increase in volatility of nitrapyrin solution | nitrapyrin without solvent |
|---|---|---|---|---|---|---|---|---|
| 0 | 100.00% | preheat | | 100.15% | preheat | | preheat | 100.00% |
| 1 | 99.75% | | | 99.54% | | | | 99.20% |
| 2 | 99.26% | | | 98.32% | | | | 98.56% |
| 3 | 98.15% | | | 96.85% | | | | 97.92% |
| 4 | 97.29% | 0.86% | 3.44% | 96.49% | 0.36% | 1.44% | 139% | 96.00% |
| 5 | 96.19% | 1.10% | 4.40% | 95.88% | 0.61% | 2.44% | 80% | 94.87% |
| 6 | 95.57% | 0.62% | 2.48% | 95.27% | 0.61% | 2.44% | 2% | 93.75% |
| 7 | 94.71% | 0.86% | 3.44% | 94.50% | 0.77% | 3.08% | 12% | 92.63% |
| 8 | 93.85% | 0.86% | 3.44% | 93.74% | 0.76% | 3.04% | 13% | 90.87% |
| 9 | 93.23% | 0.62% | 2.48% | 93.13% | 0.61% | 2.44% | 2% | 89.90% |
| 10 | 92.50% | 0.73% | 2.92% | 92.52% | 0.61% | 2.44% | 20% | 89.10% |
| Delta 3-10 | 5.65% | 0.81% | | 4.33% | 0.62% | | 30% | |
| Delta 4-10 | 4.79% | 0.68% | | 3.97% | 0.57% | | 21% | |
| Delta 5-10 | 3.69% | 0.53% | | 3.36% | 0.48% | | 10% | |
| Cumulative 3-10 | | | 22.60% | | | 17.32% | | |
| Cumulative 4-10 | | | 19.16% | | | 15.88% | | |
| Cumulative 5-10 | | | 14.76% | | | 13.44% | | |

* % increase in volatility of nitrapyrin solution compared to nitrapyrin polyanionic salt solution agricultural carrier Tests were run to determine the relative volatility of the nitrapyrin solution without polyanionic polymer

TABLE 3

| Experiment time, min. | nitrapyrin without solvent | Solvent alone | nitrapyrin sulfolane volatility ratio | nitrapyrin solution volatility rate vs. solvent alone * | nitrapyrin polymer salt solution volatility rate vs. solvent alone |
|---|---|---|---|---|---|
| 0 | 100.00% | 100.0% | | | |
| 1 | 99.20% | 99.85% | | | |
| 2 | 98.56% | 99.56% | | | |
| 3 | 97.92% | 98.68% | | | |
| 4 | 96.00% | 98.24% | | | |
| 5 | 94.87% | 97.95% | | | |
| 6 | 93.75% | 97.51% | | | |
| 7 | 92.63% | 97.51% | | | |
| 8 | 90.87% | 97.07% | | | |
| 9 | 89.90% | 96.77% | | | |
| 10 | 89.10% | 96.48% | | | |
| Delta 3-10 | | | 401% | 527% | 197% |
| Delta 4-10 | | | 392% | 272% | 226% |
| Delta 5-10 | | | 393% | 251% | 229% |
| Cumulative 3-10 | | | | | |
| Cumulative 4-10 | | | | | |
| Cumulative 5-10 | | | | | |

* the nitrapyrin solution (without polyanionic polymer) is more volatile than solvent alone.

Example 2. Formation of Solutions of Nitrapyrin Salts and Grading of Solutions

TABLE 4

Nitrapyrin salt solutions containing 20% nitrapyrin

| polyanion | # anionic groups | MW (per repeat unit), corrected for conc. | MW/charged group | g polyanion to react 1:1 with 2.00 g nitrapyrin | g solvent to be used* |
|---|---|---|---|---|---|
| malic | 2 | 134 | 67 | 0.580 | 7.420 |
| tartaric | 2 | 150 | 75 | 0.649 | 7.351 |
| etidronic | 4 | 343 | 86 | 0.742 | 7.258 |
| succinic | 2 | 118 | 59 | 0.511 | 7.489 |
| adipic | 2 | 146 | 73 | 0.632 | 7.368 |
| sebacic | 2 | 202 | 101 | 0.874 | 7.126 |
| isophthalic | 2 | 166 | 83 | 0.719 | 7.281 |
| maleic-acrylic copolymer | 1 | 126 | 126 | 1.091 | 6.909 |
| BC | 1 | 103 | 103 | 0.892 | 7.108 |
| T5 | 1 | 107 | 107 | 0.926 | 7.074 |

*dipropylene glycol, Dow PT250, Dow PT700, triethylene glycol, tripropylene glycol, propylene carbonate, triacetin, Agnique AMD810, Agnique AMD3L, Rhodiasolv ADMA10, Rhodiasolv ADM810, Rhodiasolv Polarclean. Solvents which can be used to dissolve a nitrapyrin salt include, but are not limited to: aromatic solvents, particularly alkyl substituted benzenes such as xylene or propylbenzene fractions, and mixed naphthalene and alkyl naphthalene fractions; mineral oils; kerosene; dialkyl amides of fatty acids, particularly the dimethylamides of fatty acids such as the dimethyl amide of caprylic acid; chlorinated aliphatic and aromatic hydrocarbons such as 1,1,1-trichloroethane and chlorobenzene, esters of glycol derivatives, such as the acetate of the n-butyl, ethyl, or methyl ether of diethyleneglycol and the acetate of the methyl ether of dipropylene glycol; ketones such as isophorone and trimethylcyclohexanone (dihydroisophorone); and the acetate products such as hexyl or heptyl acetate.

TABLE 5

Component Calculations and Solvent Density

| | |
|---|---|
| Nitrapyrin, moles in 2.00 g | 0.00866 |
| BC acid density, g/ml, est. | 1.23 |
| T5 acid density, g/ml, est. | 1.20 |
| Maleic-acrylic density, g/ml | 1.23 |
| Dipropylene glycol | 1.02 g/ml |
| PT700 | 1.03 g/ml |
| PT250 | 1.09 g/ml |
| Triethylene glycol | 1.13 g/ml |
| Tripropylene glycol | 1.02 g/ml |
| Propylene carbonate | 1.21 g/ml |
| Triacetin | 1.16 g/ml |
| Agnique AMD810 | 0.88 g/ml |
| Agnique AMD3L | 1.05 g/ml |
| Rhodiasolv ADMA10 | 0.88 g/ml |
| Rhodiasolv ADM810 | 0.88 g/ml |
| Rhodiasolv Polarclean | 1.04 g/ml |

TABLE 6

Grading Scale of Solutions

| | |
|---|---|
| Fully dissolved | 5 |
| Mostly dissolved | 4 |
| Mostly not dissolved | 3 |
| Not dissolved | 2 |
| Additional precipitate | 1 |

TABLE 7

Solvent Acid Combination Table; results for reaction at 20% w/w nitrapyrin

| Solvent Acid | dipropylene glycol A | PT700 B | PT250 C | triethylene glycol D | tripropylene glycol E | propylene carbonate F | triacetin G | Agnique AMD810 H | Agnique AMD3L I | Rhodiasolv ADMA10 J | Rhodiasolv ADMA810 K | Rhodiasolv Polarclean L |
|---|---|---|---|---|---|---|---|---|---|---|---|---|
| malic | 1 | 2 | 4 | 1 | 2 | 2 | 3 | 3 | 5 | 5 | 5 | 5 | 5 |
| tartaric | 2 | 2 | 2 | 1 | 1 | 2 | 2 | 2 | 5 | 5 | 5 | 5 | 5 |
| etidronic | 3 | 1 | 4 | 1 | 1 | 1 | 2 | 2 | 4 | 5 | 5 | 4 | 5 |

TABLE 7-continued

Solvent Acid Combination Table; results for reaction at 20% w/w nitrapyrin

| Solvent Acid | | dipropylene glycol A | PT700 B | PT250 C | tri-ethylene glycol D | tri-propylene glycol E | propylene carbonate F | triacetin G | Agnique AMD810 H | Agnique AMD3L I | Rhodiasolv ADMA10 J | Rhodiasolv ADMA810 K | Rhodiasolv Polarclean L |
|---|---|---|---|---|---|---|---|---|---|---|---|---|---|
| succinic | 4 | 3 | 4 | 1 | 2 | 3 | 3 | 2 | 5 | 5 | 5 | 5 | 5 |
| adipic | 5 | 2 | 3 | 1 | 3 | 4 | 3 | 3 | 5 | 5 | 5 | 5 | 5 |
| sebaric | 6 | 1 | 2 | 1 | 2 | 1 | 2 | 2 | 3 | 5 | 2 | 4 | 5 |
| isophthalic | 7 | 2 | 2 | 1 | 1 | 4 | 3 | 3 | 3 | 3 | 3 | 3 | 3 |
| maleic-acrylic copolymer | 8 | 1 | 2 | 1 | 1 | 1 | 2 | 2 | 5 | 5 | 5 | 5 | 5 |
| BC | 9 | 1 | 4 | 1 | 1 | 1 | 2 | 2 | 5 | 5 | 5 | 5 | 5 |
| T5 | 10 | 1 | 2 | 1 | 1 | 1 | 2 | 2 | 3 | 5 | 3 | 4 | 5 |

TABLE 8

Solvent acid combination, solvent volumes, 8x pipetting

| Solvent Acid | | dipropylene glycol A | PT700 B | PT250 C | tri-ethylene glycol D | tri-propylene glycol E | propylene carbonate F | triacetin G | Agnique AMD810 H | Agnique AMD3L I | Rhodiasolv ADMA10 J | Rhodiasolv ADMA810 K | Rhodiasolv Polarclean L |
|---|---|---|---|---|---|---|---|---|---|---|---|---|---|
| malic | 1 | 0.909 | 0.900 | 0.851 | 0.821 | 0.909 | 0.767 | 0.800 | 1.054 | 0.883 | 1.054 | 1.054 | 0.892 |
| tartaric | 2 | 0.901 | 0.892 | 0.843 | 0.813 | 0.901 | 0.759 | 0.792 | 1.044 | 0.875 | 1.044 | 1.044 | 0.883 |
| etidronic | 3 | 0.889 | 0.881 | 0.832 | 0.803 | 0.889 | 0.750 | 0.782 | 1.031 | 0.864 | 1.031 | 1.031 | 0.872 |
| succinic | 4 | 0.918 | 0.909 | 0.859 | 0.828 | 0.918 | 0.774 | 0.807 | 1.064 | 0.892 | 1.064 | 1.064 | 0.900 |
| adipic | 5 | 0.903 | 0.894 | 0.845 | 0.815 | 0.903 | 0.761 | 0.794 | 1.047 | 0.877 | 1.047 | 1.047 | 0.886 |
| sebaric | 6 | 0.873 | 0.865 | 0.817 | 0.788 | 0.873 | 0.736 | 0.768 | 1.012 | 0.848 | 1.012 | 1.012 | 0.856 |
| isophthalic | 7 | 0.892 | 0.884 | 0.835 | 0.805 | 0.892 | 0.752 | 0.785 | 1.034 | 0.867 | 1.034 | 1.034 | 0.875 |
| maleic-acrylic copolymer | 8 | 0.847 | 0.838 | 0.792 | 0.764 | 0.847 | 0.714 | 0.745 | 0.981 | 0.823 | 0.981 | 0.981 | 0.830 |
| BC | 9 | 0.871 | 0.863 | 0.815 | 0.786 | 0.871 | 0.734 | 0.766 | 1.010 | 0.846 | 1.010 | 1.010 | 0.854 |
| T5 | 10 | 0.867 | 0.858 | 0.811 | 0.782 | 0.867 | 0.731 | 0.762 | 1.005 | 0.842 | 1.005 | 1.005 | 0.850 |

All technical and scientific terms used herein have the same meaning. Efforts have been made to ensure accuracy with respect to numbers used (e.g., amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. A nitrapyrin complex comprising nitrapyrin complexed with a polyanion, wherein the nitrapyrin complex is formulated as an aqueous dispersion.

2. The nitrapyrin complex of claim 1, wherein the polyanion has a MW/charge ratio of 45-200; and/or has a net formal charge less than −2 in dilute aqueous solution at pH 10.

3. The nitrapyrin complex of claim 2 wherein the polyanion comprises a polyanionic polymer.

4. The nitrapyrin complex of claim 3, where the polyanionic polymer comprises a random copolymer having at least two repeat units including at least one each of type B and type C repeat unites, and optionally one or more different type G repeat units, wherein a) the type B repeat units are independently selected from the group consisting of repeat units derived from substituted and unsubstituted monomers of maleic acid, maleic anhydride, fumaric acid, fumaric anhydride, mesaconic acid, mesaconic, mixtures of the foregoing, and any isomers, esters, acid chlorides, and partial or complete salts of any of the foregoing, wherein type B repeat units may be substituted with one or more $C_1$-$C_6$ straight or branched chain alkyl groups substantially free of ring structures and halo atoms, and wherein the salts have salt-forming cations selected from the group consisting of metals, amines, and mixtures thereof, b) the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more $C_1$-$C_6$ straight or branched chain alkyl groups substantially free of ring structures and halo atoms, and wherein the salts have salt-forming cations selected from the group consisting of metals, amines, and mixtures thereof, and c) the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more $C_1$-$C_6$ straight or branched chain alkyl groups substantially free of ring structures and halo atoms, and wherein the salts of the type G repeat units have salt-forming cations selected from the group consisting of metals, amines, and mixtures thereof, and wherein at least about 90 mole percent of the repeat units therein are selected from the group consisting of type B, C, and G repeat units, and mixtures thereof, and, wherein the polyanionic polymer contains no more than about 10 mole percent of any of (i) non-carboxylate olefin repeat units, (ii) ether repeat units, and (iii) non-sulfonated monocarboxylic repeat units.

5. The nitrapyrin complex of claim 4, wherein the polyanionic polymer consists of one type B repeat unit derived from maleic acid, one type C repeat unit derived from itaconic acid, and two type G repeat units respectively derived from methallylsulfonic acid and allylsulfonic acid.

6. The nitrapyrin complex of claim 4, wherein the polyanionic polymer has a repeat unit molar composition of:
 1-70 mole percent type B repeat units, 1-80 mole percent type C repeat units, and 0.1-65 mole percent type G repeat units; or
 20-65 mole percent type B repeat units, 15-75 mole percent type C repeat units, and 1-35 mole percent type G repeat units; or
 35-55 mole percent type B repeat units, 20-55 mole percent type C repeat units, and 1-25 mole percent methallylsulfonic repeat units, and 1-20 mole percent allylsulfonic repeat units; or
 45 mole percent maleic repeat units, 50 mole percent itaconic repeat units, 4 mole percent methallylsulfonic repeat units, and 1 mole percent allylsulfonic repeat units; or
 45 mole percent maleic repeat units, 35 mole percent itaconic repeat units, 15 mole percent methallylsulfonate repeat units, and 5 mole percent allylsulfonate repeat units.

7. The nitrapyrin complex of claim 4, wherein the polyanionic polymer is a copolymer or homopolymer consisting of B type and C type repeat units.

8. The nitrapyrin complex of claim 4, wherein the polyanionic polymer is a copolymer consisting of maleic and itaconic repeat units and has an average molecular weight of about 100-50,000 Da.

9. The nitrapyrin complex of claim 3, wherein the polyanionic polymer contains at least 80 mole percent repeat units containing at least one anionic group.

10. The nitrapyrin complex of claim 3, wherein the polyanionic polymer has a lower vapor pressure as compared to the vapor pressure of nitrapyrin.

11. The nitrapyrin complex of claim 3, wherein the polyanionic polymer is selected from the group consisting of a random copolymer a terpolymer and a tetrapolymer.

12. The nitrapyrin complex of claim 2, wherein the polyanion comprises a non-polymeric polyanion.

13. The nitrapyrin complex of claim 12, wherein the non-polymeric polyanion comprises a di-, tri-, tetra-, penta-, hexa-, hepta-, octa-, nona-, deca-aliphatic carboxyl, an aromatic carboxyl, a di-, tri-, tetra-, penta-, hexa-, hepta-, octa-, nona-, deca-sulfonate, or a di-, tri-, tetra-, penta-, hexa-, hepta-, octa-, nona-, deca-phosphonate or an aliphatic.

14. The nitrapyrin complex of claim 13, wherein the non-polymeric polyanion is selected from the list consisting of: malic acid, tartaric acid, etidronic acid, succinic acid, adipic acid, isophthalic acid, aconitic, trimesic, biphenyl-3, 3',5,5'-tetracarboxylic acid, furantetracarboxylic acid, sebacic acid, azelaic acid, isoterephtalic acid, pyromellitic acid, and mellitic acid.

15. A composition comprising the nitrapyrin complex of claim 1 and an organic solvent, wherein the solvent is selected from the group consisting of: aromatic solvent, alkyl substituted benzene, xylene, propylbenzene, mixed naphthalene and alkyl naphthalene, mineral oil, kerosene, dialkyl amide of fatty acid, dimethylamide of fatty acid, dimethyl amide of caprylic acid, chlorinated aliphatic hydrocarbon, aromatic hydrocarbon, 1,1,1-trichloroethane, chlorobenzene, ester of glycol derivative, n-butyl ether of diethyleneglycol, ethyl ether of diethyleneglycol, methyl ether of diethyleneglycol, acetate of the methyl ether of dipropylene glycol, ketone, isophorone, trimethylcyclohexanone (dihydroisophorone), acetate, hexyl acetate, heptyl acetate, aromatic 100 (CAS No: 64742-95-6), aromatic 200 (CAS No. 64742-94-5), sulfones, glycols, polyglycol, dipropylene glycol, Dow PT250, Dow PT700, PT250, triethylene glycol, tripropylene glycol, propylene carbonate, triacetin, Agnique AMD810, Agnique AMD3L, Rhodiasolv ADMA10, Rhodiasolv ADMA810, Rhodiasolv Polarclean, and mixtures thereof.

16. The composition of claim 15, wherein said concentration of nitrapyrin complex is from about 20% to about 50% wt/wt.

17. A composition comprising an agricultural product and a nitrapyrin complex of claim 1, wherein the agricultural product is a fertilizer and the nitrapyrin complex is present at a level of about 0.001 to about 20 g per 100 g of fertilizer.

18. A composition comprising an agricultural product and a nitrapyrin complex of claim 1, wherein the agricultural product is a seed and wherein the seed is coated with the nitrapyrin complex to form a coated seed product that after drying thereof provides a level of nitrapyrin from about 0.001-10% by weight, based upon the total weight of the coated seed product.

19. A composition comprising:
a nitrapyrin complexed with a polyanionic polymer, wherein said polymer comprises:
recurring polymeric subunits each made up of at least two different moieties individually and respectively taken from the group consisting of B and C moieties, wherein moiety B is a dicarboxylic moiety of the general formula

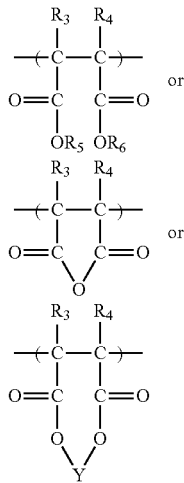

and moiety C is a dicarboxylic moiety of the general formula

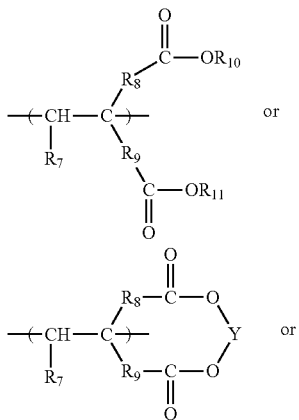

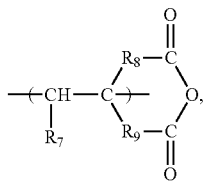

wherein each $R_7$ is individually and respectively selected from the group consisting of H, OH, $C_1$-$C_{30}$ straight, branched chain and cyclic alkyl or aryl groups, $C_1$-$C_{30}$ straight, branched chain and cyclic alkyl or aryl based ester groups, $R'CO_2$ groups, $OR'$ groups and COOS groups, wherein $R'$ is selected from the group consisting of $C_1$-$C_{30}$ straight, branched chain and cyclic alkyl or aryl groups and X is selected from the group consisting of H, the alkali metals, $NH_4$ and the $C_1$-$C_4$ alkyl ammonium groups, $R_3$ and are individually and respectively selected from the group consisting of H, $C_1$-$C_{30}$ straight, branched chain and cyclic alkyl or aryl groups, $R_5$, $R_6$, $R_{10}$ and $R_{11}$ are individually and respectively selected from the group consisting of H, the alkali metals, $NH_4$ and the $C_1$-$C_4$ alkyl ammonium groups, Y is selected from the group consisting of Fe, Mn, Mg, Zn, Cu, Ni, Co, Mo, V and Ca, and $R_8$ and $R_9$ are individually and respectively selected from the group consisting of nothing (i.e., the groups are nonexistent), $CH_2$, $C_2H_4$, and $C_3H_6$, each of said moieties having or being modified to have a total of two COO groups therein, all of the moieties making up the polymer being dicarboxylic moieties; and
an organic solvent, wherein the organic solvent is selected from the group consisting of: aromatic 100 (CAS No: 64742-95-6), aromatic 200 (CAS No. 64742-94-5), sulfones, glycols, polyglycol, dipropylene glycol, Dow PT250, Dow PT700, triethylene glycol, tripropylene glycol, propylene carbonate, triacetin, Agnique AMD810, Agnique AMD3L, Rhodiasolv ADMA10, Rhodiasolv ADMA810, Rhodiasolv Polarclean, and mixtures thereof,
wherein the composition is formulated as an aqueous dispersion.

20. The composition of claim 19, wherein said recurring polymeric subunits are made up of B and C moieties, wherein $R_3$ and $R_4$ are each H, and $R_5$ and $R_6$ are Na; and/or $R_4$ is individually and respectively selected from the group consisting of H, OH and $C_1$-$C_4$ straight and branched chain alkyl groups, $R_5$, $R_6$ and X are individually and respectively selected from the group consisting of the alkali metals; and/or said polymer being complexed with a metal ion selected from the group consisting of Fe, Mn, Mg, Zn, Cu, Ni, Co, Mo, V and Ca.

* * * * *